US007871766B2

(12) United States Patent
Pauly et al.

(10) Patent No.: US 7,871,766 B2
(45) Date of Patent: Jan. 18, 2011

(54) COSMETIC AND/OR DERMOPHARMACEUTICAL PREPARATIONS CONTAINING NATIVE PROTEINS FROM THE PLANT *ARGANIA SPINOSA*

(75) Inventors: Gilles Pauly, Nancy (FR); Florence Henry, Villers-les-Nancy (FR); Philippe Moser, Essey les Nancy (FR); Zoubida Charrouf, Rabat R.P. (MA)

(73) Assignee: Cognis IP Management GmbH, Duesseldorf (DE)

( * ) Notice: Subject to any disclaimer, the term of this patent is extended or adjusted under 35 U.S.C. 154(b) by 1489 days.

(21) Appl. No.: 10/450,019

(22) PCT Filed: Nov. 28, 2001

(86) PCT No.: PCT/EP01/13886
§ 371 (c)(1),
(2), (4) Date: Jun. 6, 2003

(87) PCT Pub. No.: WO02/45729
PCT Pub. Date: Jun. 13, 2002

(65) Prior Publication Data
US 2004/0042996 A1 Mar. 4, 2004

(30) Foreign Application Priority Data
Dec. 6, 2000 (EP) .................................. 00440318

(51) Int. Cl.
C12Q 1/68 (2006.01)
A01N 65/00 (2009.01)
A61K 8/02 (2006.01)
(52) U.S. Cl. ......................... 435/6; 424/725; 424/401
(58) Field of Classification Search .................... 435/6; 424/725, 78.03, 74, 769, 70.1, 745, 750, 424/764, 765, 775, 776; 426/31
See application file for complete search history.

(56) References Cited
U.S. PATENT DOCUMENTS

| 4,172,887 | A | 10/1979 | Vanlerberghe et al. |
| 5,705,169 | A | 1/1998 | Stein et al. |
| 5,730,960 | A | 3/1998 | Stein et al. |
| 5,945,091 | A | 8/1999 | Habeck et al. |
| 6,193,960 | B1 | 2/2001 | Metzger et al. |

FOREIGN PATENT DOCUMENTS

| DE | 1 165 574 | | 8/1960 |
| DE | 2 024 051 | | 5/1970 |
| DE | 197 56 377 | | 12/1997 |
| DE | 197 12 033 | | 9/1998 |
| EP | 0 693 471 | B1 | 1/1996 |
| EP | 0 694 521 | B1 | 1/1996 |
| EP | 0 818 450 | B1 | 1/1998 |
| FR | 2 252 840 | | 11/1974 |
| FR | 2 500 306 | | 2/1981 |
| FR | 2 553 788 | | 10/1983 |
| FR | 2 724 663 | | 9/1994 |
| FR | 2 756 183 | | 11/1996 |
| FR | 2756183 | A1 * | 5/1998 |
| GB | 962919 | | 7/1964 |
| GB | 1333475 | | 10/1973 |
| JP | 60 149511 | | 7/1985 |
| JP | 02/204417 | | 8/1990 |
| JP | 02/204495 | | 8/1990 |
| JP | 03/005423 | | 1/1991 |
| JP | 03/093782 | | 3/1991 |
| JP | 03/255015 | | 11/1991 |
| JP | 04/029934 | | 1/1992 |
| WO | WO 01/82885 | | 11/2001 |

OTHER PUBLICATIONS

Translation of FR 2756183 (Nov. 25, 1996).*
Suttie, J. Intorduction to Biochemistry, Second Edition, 1977. Holt, Rinehart and Winston (USA): University of Wisconsin, p. 56.*
Green, J. The Herbal Medicine-Maker's Handbook: A Home Manual, 2000. The Crossing Press, U.S.A, pp. 96.*
Alaoui et al. ,"Activité analgésique et anti-inflammatoire des saponines d'Argania spinosa" Annales Pharmaceutiques Francaises, vol. 56, No. 5, 1998 pp. 220-228, XP-000995497.
Berrada et al. ,"Mise en évidence expérimente des effets antihypertenseurs et hypocholestérolémiants de l'huile d'Argan, Argania sideroxylon" Therapie, vol. 55, No. 3, 2000, pp. 375-378, XP-000939171.
Charrouf et al. ,"Triterpenes et sterols extraits de la pulpe d'argania spinosa (L.), sapotaceae", Plantes medicinales et Phytotherapie vol. 25, No. 2-3,1991,pp. 112-117 XP000619575.
Alaoui et al. ,"Conservation Study of the Argan Oil by Thermogravimetry",Asian Journal of Chemistry vol. 13, No. 1, 2001 pp. 144-150 XP-001062010.
Bellakhdar et al., "Repertory of standard herbal drugs in the Moroccan pharmacopoea", Journal of Ethnopharmacology vol. 35, No. 2, 1991, pp. 123-143 XP-001068322.
Schar, M.P., "Argan Oil", Euro Cosmet, vol. 5, 1999, pp. 45-47; XP-001062004.
von Bruchhausen et al., Hagers Handbuch der pharmazeutischen Praxis, vol. 5. Bd. 2, 1991, pp. 1026-1030, Springer Verlag, Berlin Heidelberg-New York.
P. Finkel, "Formulierung kosmetischer Sonnenschutzmittel", SÖFW-Journal, 122, (1996), pp. 543-546 & 548.

(Continued)

Primary Examiner—Michele Flood

(57) ABSTRACT

A cosmetic and/or dermopharmaceutical composition containing an extract of native proteins derived from the plant *Argania spinosa*.

12 Claims, No Drawings

OTHER PUBLICATIONS

P. Finkel, "Formulierung kosmetischer Sonnenschutzmittel", Parfumerie und Kosmetik, 80, No. 3 (1999), pp. 10-12, 14-16.

J.Falbe, "Surfactants in Consumer Products", Springer Verlag, Berlin, (1987), pp. 54-124.

Falbe, "Katalysatoren, Tenside und Mineralöladditive" (Catalysts, Surfactants and Mineral Oil Additives), Thieme Verlag, Stuttgart, (1978), pp. 123-217.

R. Lochhead et al., "Encyclopedia of Polymers and Thickeners for Cosmetics", Cosmetics & Toiletries, vol. 108, (May 1993), pp. 95-135.

C. Todd et al., "Volatile silicone fluids for cosmetic formulations", Cosmetics and Toiletries, vol. 91, (Jan. 1976), pp. 29-32.

"Kosmetische Färbemittel", Farbstoffkommission der Deutschen Forschungsgemeinschaft, Verlag Chemie, Weinheim, (1984), pp. 81-106.

Denizot et al.; "Rapid colorimetric assay for cell growth and survival", J. Immunol. Methods, vol. 89, 1986, pp. 271-277.

M. Bradford, "A rapid and sensitive method for the quantitation of microgram quantities of protein utilizing the principle of protein-dye binding", Anal. Biochem., vol. 72, 1977, pp. 248-254.

Hissin et al., "A fluorometric method for determination of oxidized and reduced Glutathione in tissues", Analytical Biochemistry, vol. 74, 1976, pp. 214-218, 222-226.

Okada et al.,"Heat-labile glucose-6-phosphate Dehydrogenase in Cultured Fibroblasts from Patients with De Sanctis-Cacchione Syndrome", Arch. Dermatol. Res., vol. 271 (3), 1981, pp. 341-346.

Desaulniers "Optimization of an MCF7-E3 Cell Proliferation Assay and Effects of Environmental Pollutants and Industrial Chemicals", Toxicology in Vitro 12, 1998, pp. 409-422.

Fragrance Journal, 2005, vol. 33, No. 7, pp. 47-52 ("A" category) (abstract).

Fragrance Journal, 2005, vol. 33, No. 7, pp. 119-120 ("A" category).

R. Maurin, L'huile d'Argan *Argania spinosa* (L.) Skeels Sapotaceae, Revue Francaise des Corps Gras, vol. 39, No. 5-6, pp. 139-146. (Abstract).

Tahrouch et al., Polyphenol investigation of *Argania spinosa* (Sapotaceae) endemic tree from Morocco, Acta Botanica Gallica, 2000, vol. 147, pp. 225-232. XP-000996078.

* cited by examiner

COSMETIC AND/OR DERMOPHARMACEUTICAL PREPARATIONS CONTAINING NATIVE PROTEINS FROM THE PLANT *ARGANIA SPINOSA*

BACKGROUND OF THE INVENTION

This application is a 371 of PCT/EP01/13886 filed Nov. 28, 2001.

The invention is in the field of care substances and relates to preparations comprising native proteins from the plant *Argania spinosa*, and to the use of native proteins from the plant *Argania spinosa* as novel skin care and hair care agents.

Cosmetic preparations are available to the consumer nowadays in a large number of combinations. In this connection, it is not only expected that these cosmetics demonstrate a certain care effect or overcome a certain deficiency, but demand is more and more often for products which have several properties simultaneously and thus exhibit an improved performance spectrum. Of particular interest are substances which both represent active ingredients which impart, for example, care, revitalizing properties which protect against aging phenomena for skin and/or hair, and also simultaneously have a positive influence on or at least do not impair the technical properties of the cosmetic product, such as storage stability, photo stability and ability to be formulated. In this connection, good skin compatibility and particularly the use of natural products is additionally requested by customers. In addition, it is desirable, by combining already known active ingredients, or by discovering new fields of use for classes of substances which are already known, to obtain significantly better products. However, a disadvantage often exists here that a combination of active ingredients is only obtained if different plant extracts are used simultaneously in varying quantitative ratios.

Extracts from plants and their ingredients are being used more and more often in cosmetics and pharmacy. Plant extracts have been used for many years in a very wide variety of cultures for medicinal and also even for cosmetic purposes. Often, only very specific individual effects for these plant extracts were known, and the field of use was very limited.

DESCRIPTION OF THE INVENTION

The object of the present patent application was to provide cosmetic and/or dermopharmaceutical preparations which permit a use in cosmetics or else pharmacy and, as well as care properties have primarily improved moisture-regulating and protecting properties for human skin and/or hair and at the same time exhibit a preventative and healing effect in cases of skin aging phenomena, can have a reactivating and revitalizing effect and can be used as protection against UV radiation.

A further object of the present patent application was to provide preparations which comprise active ingredients from renewable raw materials and at the same time can be used widely as care agents in cosmetics both in skin cosmetics and also in hair care.

The invention provides preparations which comprise native proteins from the plant *Argania spinosa* as care agents for skin and hair.

Surprisingly, it has been found that by using native proteins from the plant *Argania spinosa*, products are obtained which simultaneously have good care and protecting properties for skin and hair, and also have a high skin compatibility. The compositions obtained in this way are characterized by particularly good effects in skin cosmetics. As well as moisture-regulating and protecting effects, they also exhibit a preventative and healing effect in cases of skin aging phenomena and a revitalizing and reactivating activity on skin and hair.

These multiple fields of use of the agents according to the invention from the renewable raw material of the plant *Argania spinosa* makes it very attractive for the market and for the consumer. The complex object of the invention was thus achieved through the use of native proteins from the plant *Argania spinosa*.

For the purposes of the invention, the term preparations is used synonymously with the term agents or care agents.

For the purposes of the present invention, the term plants is understood as meaning whole plants and also parts of plants (seeds, leaves, roots, flowers), and mixtures thereof.

*Argania spinosa*

The extracts to be used according to the invention are obtained from plants of the Sapotaceae family, specifically from *Argania spinosa*. This plant is a tree reminiscent of the olive tree which is found predominantly in Morocco on the west side of the Atlas mountain range. On its knurled branches and thorny twigs, it forms berries of the size and shape of olives with one to two seeds. The oil from the seeds, which has a nut-like taste, is used inter alia as a food oil.

Proteins

For the purposes of the invention, proteins are understood as meaning those which can be isolated from the plant *Argania spinosa*. Proteins form the active enzymes in all cell nuclei and provide the reserve for the formation of new enzymes. For the reason, they are an important constituent of plants and are therefore found in all parts of plants. Particular preference is given to the extraction of the seeds, in particular the defatted seeds. Accordingly, a particular embodiment of the invention is preparations which comprise native proteins which are obtained from an extract of the seeds, in particular of the defatted seeds, of *Argania spinosa*.

For the purposes of the invention, the preferred extraction of the defatted seeds is understood as meaning that preferably the residue—a type of cake—is extracted from the extraction to obtain oil from the seeds of *Argania spinosa*. This residue from the extraction for producing oil which is to be extracted in preference comprises 3 to 10% by weight of residual oil. The proteins according to the invention are removed from this residue as completely as possible from the oil which still remains. As well as proteins, further substances which are naturally occurring in the plants *Argania spinosa* can also be coextracted, which can be extracted under the same conditions.

In a further embodiment of the invention, the preparations according to the invention comprise native proteins which are obtained by aqueous extraction at a pH of less than or equal to 12, preferably between 3.5 and 6.5, in particular either between 5.5 and 6.5 or between 3.5 and 5.5 and optionally by subsequent drying, for example spray- or freeze-drying. The chosen pH range is dependent on the protein fraction to be isolated.

The native proteins which can be extracted from the plant *Argania spinosa*, in particular from the seeds of the plant, can have molecular weights between 10 000 Da and greater than 500 000 Da. Preferably, they can be divided into the following groups of molecular weight ranges. It is possible to extract native proteins with a molecular weight greater than 500 000 Da, native proteins with a molecular weight in the range from 170 000 to 250 000 Da and native proteins with a molecular weight in the range from 10 000 to 18 000 Da.

Accordingly, further embodiments of the invention firstly relate to preparations which comprise native proteins whose molecular weight is greater than 500 000 Da, to preparations which comprise native proteins whose molecular weight is in the range from 170 000 Da to 250 000 Da, preferably in the range from 170 000 Da to 210 000 Da, and to preparations which comprise native proteins whose molecular weight is in the range from 10 000 to 18 000, preferably in the range from 13 000 to 16 000.

The proportion of native proteins, calculated on the basis of the dry weight of the extract, is between 20 and 60% by weight, in particular 35 to 55% by weight. Accordingly, a further particular embodiment of the invention is preparations which comprise native proteins in the form of an extract with an active substance content in the range from 20 to 85% by weight, in particular 35 to 55% by weight or 60 to 85% by weight, calculated on the basis of the dry weight, depending on the extraction method.

Extraction

The extracts to be used according to the invention are prepared by customary methods of extraction of plants or parts of plants. With regard to the suitable conventional extraction methods, such as maceration, remaceration, digestion, agitation maceration, fluidized-bed extraction, ultrasound extraction, countercurrent extraction, percolation, repercolation, evacolation (extraction under reduced pressure), diacolation and solid-liquid extraction under continuous reflux which is carried out in a Soxhlet extractor, each of which is known to the person skilled in the art and any of which can be used in principle, reference may be made by way of example to Hagers Handbuch der Pharmazeutischen Praxis, ($5^{th}$ edition, Vol. 2, pp. 1026-1030, Springer Verlag, Berlin-Heidelberg-New York 1991). Starting material which may be used are fresh or dried plants or parts of plants, although usually the starting materials are plants and/or parts of plants which can be mechanically comminuted prior to extraction. In this connection, all comminution methods known to the person skilled in the art are suitable, mention being made by way of example to comminution using a device containing blades. Preference is given to extracting the residue from the oil production from the seeds of the plant.

Solvents which can be used for carrying out the extractions are preferably organic solvents, water or mixtures of organic solvents and water, in particular low molecular weight alcohols, esters, ethers, ketones or halogen-containing hydrocarbons with greater or lesser water contents (distilled or undistilled), preferably aqueous, alcoholic solutions with greater or lesser water contents. Particular preference is given to the extraction with water, methanol, ethanol, propanol, butanol and isomers thereof, propylene glycols, polyethylene glycols, and mixtures thereof. The extraction usually takes place at 20 to 100° C., preferably at 80 to 100° C., in particular at the boiling temperature of the solvents or solvent mixtures. In one possible embodiment, the extraction is carried out under an inert gas atmosphere to avoid oxidation of the ingredients of the extract. The extraction times are adjusted by the person skilled in the art depending on the starting material, the extraction method, the extraction temperature, the ratio of solvent to raw material, etc. After the extraction, the resulting crude extracts can optionally be subjected to further customary steps, such as, for example, purification, concentration and/or decoloration. If desired, the extracts prepared in this way can, for example, be subjected to selective removal of individual undesired ingredients. The extraction can be carried out to any desired degree of extraction, but is usually carried out exhaustively.

The present invention encompasses the finding that the extraction conditions and also the yields of the end extracts can be chosen depending on the desired field of use.

The amount of plant extracts used in said preparations is governed by the concentration of the individual ingredients and by the type of applications of the extracts. The total amount of the plant extract comprising the native proteins which is present in the preparations according to the invention is usually 0.01 to 25% by weight, preferably 0.03 to 5% by weight, in particular 0.03 to 0.6% by weight, based on the preparations, with the proviso that the quantitative amounts add up to 100% by weight with water and optionally further auxiliaries and additives.

The total proportion of auxiliaries and additives may be 1 to 50% by weight, preferably 5 to 40% by weight, based on the end preparation of the cosmetic and/or dermopharmaceutical preparations. The preparations can be prepared by customary cold or hot processes; preference is given to using the phase-inversion temperature method.

For the purposes of the invention, active substance refers to the proportion of substances and also auxiliaries and additives which are present in the agent, with the exception of the additionally added water.

The invention further provides for the use of native proteins from extracts of the plant *Argania spinosa* as care agents for the skin and/or the hair. This type of use includes both agents with a cosmetic effect and also with a dermopharmaceutical effect.

Care Agents:

For the purposes of the invention, care agents are understood as meaning care agents for skin and hair. These care agents include, inter alia, cleansing and restorative action for skin and hair.

Application can be topical or orally in the form of tablets, dragees, capsules, juices, solutions and granules.

The preparations according to the invention moreover exhibit an excellent skin care action coupled with simultaneously high skin compatibility. In addition, they exhibit good stability, in particular toward oxidative decomposition of the products. The preparations have a large number of cosmetic and dermopharmaceutical effects. The invention therefore further provides for the use of native proteins from extracts of the plant *Argania spinosa*

- as care agents for skin and/or hair;
- as moisture-regulating humectant;
- as agent for strengthening the skin barrier functions;
- as skin-smoothing and skin-stabilizing agent;
- as sunscreen, in particular against UVA radiation and/or against UVB radiation;
- as agent against skin aging;
- as revitalizing and restructuring agent for skin and/or hair;
- as active ingredients for the preparation of a composition for increasing the metabolic G6PDH activity.

For the purposes of the invention, the native proteins from extracts of the plant *Argania spinosa* act as moisture-regulating humectants. For the purposes of the invention, skin care agents are understood as including those which serve to regulate the moisture of the skin. For the purposes of the invention, this corresponds to the definition of a moisturizer. There are substances or mixtures of substances which give cosmetic and/or dermopharmaceutical preparations the property, following application and distribution on the surface of the skin, of reducing the moisture release of the *Stratum corneum* (horny layer).

The humectants according to the invention comprise native proteins from extracts of the plant *Argania spinosa*. Further humectants may, for example, be present in combination with the native proteins from the plant extract, such as:

- polyglycerol fatty acid esters based on fatty acids having 12-18 carbon atoms, e.g. tetraglyceryl mono-oleate, triglyceryl diisostearate;
- pyroglutamic acid or L-arginine pyroglutamate, L-lysine pyroglutamate;
- mixtures of amino acids, such as, for example, L-alanine, L-arginine, L-serine, L-threonine;
- propylene glycol
- acetamide
- polysaccharides or hyaloronic acid
- ricinous oil ethers and sorbitan esters as described in JP60149511 (Lion Corp)

Sunscreens or UV Light Protection Factors

The native proteins from extracts of the plant *Argania spinosa* act as sunscreens for the purposes of the invention.

For the purposes of the invention, sunscreens or UV light protection factors are the terms used for light protection agents which are useful for protecting the human skin against harmful influence of direct and indirect solar radiation. The ultraviolet radiation from the sun which is responsible for tanning the skin is divided into the sections UV-C (wavelengths 200-280 nm), UV-B (280-315 nm) and UV-A (315-400 nm).

The pigmentation of normal skin under the influence of solar radiation, i.e. the formation of melanins, is brought about by UV-B and UV-A in different ways. Irradiation with UV-A rays ("long-wave UV") results in the darkening of the melanin bodies already present in the epidermis, without harmful influences being evident. This is different in the case of so-called "short-wave UV" (UV-B). This brings about the formation of so-called delayed pigment as a result of the new formation of melanin granules. However, before the (protecting) pigment is formed, the skin is subject to the effect of unfiltered radiation which, depending on the exposure time, can lead to the formation of skin redness (erythema), skin inflammations (sunburn) and even blisters.

The UV absorbers or light filters used, which thus convert the UV radiation into harmless heat, are native proteins from extracts of the plant *Argania spinosa*, these can additionally be present in combination with further sunscreen or UV light protection factors.

These further UV light protection factors are, for example, organic substances (light protection filters) which are liquid or crystalline at room temperature and which are able to absorb ultraviolet rays and give off the absorbed energy again in the form of longer-wavelength radiation, e.g. heat. UVB filters can be oil-soluble or water-soluble. Examples of oil-soluble substances are:

- 3-benzylidenecamphor or 3-benzylidenenorcamphor and derivatives thereof, e.g. 3-(4-methylbenzylidene)camphor, as described in EP 0693471 B1;
- 4-aminobenzoic acid derivatives, preferably 2-ethyl-hexyl 4-(dimethylamino)benzoate, 2-octyl 4-(dimethylamino)benzoate and amyl 4-(dimethylamino)benzoate;
- esters of cinnamic acid, preferably 2-ethylhexyl 4-methoxycinnamate, propyl 4-methoxycinnamate, isoamyl 4-methoxycinnamate, 2-ethylhexyl 2-cyano-3,3-phenyl-cinnamate (octocrylene);
- esters of salicylic acid, preferably 2-ethylhexyl salicylate, 4-isopropylbenzyl salicylate, homomenthyl salicylate;
- derivatives of benzophenone, preferably 2-hydroxy-4-methoxybenzophenone, 2-hydroxy-4-methoxy-4'-methyl-benzophenone, 2,2'-dihydroxy-4-methoxybenzophenone;
- esters of benzalmalonic acid, preferably di-2-ethylhexyl 4-methoxybenzmalonate;
- triazine derivatives, such as, for example, 2,4,6-trianilino (p-carbo-2'-ethyl-1'-hexyloxy)-1,3,5-triazine and octyltriazone, as described in EP 0818450 A1 or dioctylbutamidotriazone (Uvasorb® HEB);
- propane-1,3-diones, such as, for example, 1-(4-tert-butylphenyl)-3-(4'-methoxyphenyl)propane-1,3-dione;
- ketotricyclo(5.2.1.0)decane derivatives, as described in EP 0694521 B1.

Suitable water-soluble substances are:

- 2-phenylbenzimidazole-5-sulfonic acid and the alkali metal, alkaline earth metal, ammonium, alkylammonium, alkanolammonium and glucammonium salts thereof;
- sulfonic acid derivatives of benzophenones, preferably 2-hydroxy-4-methoxybenzophenone-5-sulfonic acid and its salts;
- sulfonic acid derivatives of 3-benzylidenecamphor, such as, for example, 4-(2-oxo-3-bornylidenemethyl)-benzenesulfonic acid and 2-methyl-5-(2-oxo-3-bornylidene) sulfonic acid and salts thereof.

Suitable typical UV-A filters are, in particular, derivatives of benzoylmethane, such as, for example, 1-(4'-tert-butylphenyl)-3-(4'-methoxyphenyl)propane-1,3-dione, 4-tert-butyl-4'-methoxydibenzoylmethane (Parsol 1789), 1-phenyl-3-(4'-isopropylphenyl)propane-1,3-dione, and enamine compounds, as described in DE 19712033 A1 (BASF). The UV-A and UV-B filters can of course also be used in mixtures. As well as said soluble substances, insoluble light protection pigments, namely finely dispersed metal oxides or salts, are also suitable for this purpose. Examples of suitable metal oxides are, in particular, zinc oxide and titanium oxide and also oxides of iron, zirconium, silicon, manganese, aluminum and cerium, and mixtures thereof. Salts which may be used are silicates (talc), barium sulfate or zinc stearate. The oxides and salts are used in the form of the pigments for skin care and skin-protective emulsions and decorative cosmetics. The particles here should have an average diameter of less than 100 nm, preferably between 5 and 50 nm and in particular between 15 and 30 nm. They can have a spherical shape, but it is also possible to use particles which have an ellipsoidal shape or a shape deviating in some other way from the spherical form. The pigments can also be surface-treated, i.e. hydrophilicized or hydrophobicized. Typical examples are coated titanium dioxides, such as, for example, titanium dioxide T 805 (Degussa) or Eusolex® T2000 (Merck). Suitable hydrophobic coating agents are here primarily silicones and, specifically in this case, trialkoxyoctylsilanes or dimethicones. In sunscreens, preference is given to using micro- or nanopigments. Preference is given to using micronized zinc oxide. Further suitable UV light protection filters are given in the review by P. Finkel in SÖFW-Journal 122, 543 (1996) and Parf. Kosm. 3, 11 (1999).

The native proteins from extracts of the plant *Argania spinosa* are effective, for the purposes of the invention, against the damage to fibroblasts and/or keratinocytes by UVA radiation and/or UVB radiation.

UVA rays penetrate into the dermis, where they lead to oxidative stress, which is demonstrated by a lipoperoxidation of the cytoplasma membranes. The lipoperoxides are degraded to malonaldialdehyde (MDA), which will crosslink many biological molecules such as proteins and nucleic bases (enzyme inhibition or mutagenesis). The extracts of the plant *Argania spinosa* according to the invention significantly reduce the degree of MDA in human fibroblasts, which is induced by UVA rays and thus exhibit a high capacity for reducing harmful effects of oxidative stress on the skin.

UVB rays trigger inflammation through activation of an enzyme, namely phospholipase A2 or PLA2. This inflammation (erythema, odema) is triggered by the removal of arachidonic acid from the phospholipids in the plasma membrane by the phospholipase. Arachidonic acid is the precursor of prostaglandins, which cause inflammation and cell membrane damage; the prostaglandins E2 (=PGE2) are formed by cyclooxygenase. The degree of release of the cytoplasm enzyme LDH (lactate dehydrogenase) in human keratinocytes serves as a marker for cell damage.

The native proteins from extracts of the plant *Argania spinosa* according to the invention reduce the effect of UBV radiation on the number of keratinocytes and on the content of released LDH. Accordingly, the extracts have the ability to reduce the damage to some membranes caused by UBV radiation.

For the purposes of the invention, the native proteins from extracts of the plant *Argania spinosa* are effective against skin aging, in particular against every type of line formation and wrinkling. Another name for this type of care agent is also antiaging agent. The uses include a slowing of aging processes of the skin. The aging phenomena can have a very wide variety of causes. In particular, these aging phenomena can be based on apoptosis, caused by UV radiation or by damage to the skin induced by the destruction of proteins endogenous to the skin such as, for example, collagen or elastane.

For the purposes of the invention, the native proteins from extracts of the plant *Argania spinosa* are effective as protective and restorative care agents with revitalizing and reactivating activities for the skin and/or hair. This type of use of these care agents has a positive effect, for example against the negative effect of environmental pollution on skin and/or hair by reactivating the natural functions of skin and/or hair and making the skin and/or hair more resistant. The revitalizing and reactivating activity of native proteins from extracts of the plant *Argania spinosa* counteracts apoptosis. The teaching according to the invention includes the finding that the native proteins from extracts of the plant *Argania spinosa* act as a skin-smoothing and skin-stabilizing agent.

For the purposes of the invention, apoptosis is understood as being the targeted cell death of certain undesired or damaged cells. It is an active process of the cells (suicide on command). Apoptosis is started by an oxidative stress (UV radiation, inflammation), by a lack of growth factors or by toxic substances (pollutants, genotoxic substances etc.). During skin aging, a lack of growth factors in the skin may, for example, lead to induced apoptosis of the skin cells. In the cells affected by apoptosis, the specific enzyme endonuclease breaks down the nuclear DNA and locks the DNA fragments into the cytoplasm. For the purposes of the invention, growth factors are understood as meaning in principle all those which are endogenous to the body or introduced from outside which stimulate growth of skin and hair cells. These include, for example, hormones and chemical mediators or signal molecules. They are, for example, polypeptide growth factors or glycoprotein growth factors. Mention may be made here of the epidermal growth factor (EGF), which consists of 53 amino acids and thus represents a polypeptide growth factor, or fibrillin, which is one of the glycoproteins. Further growth factors are, for example, urogastron, laminin, follistatin and heregelin.

The native proteins from extracts of the plant *Argania spinosa* according to the invention can be used as active ingredients for the preparation facilitating the increase in the metabolic G6PDH activity since they increase, as has been demonstrated, the enzymatic activity of this enzyme important for the metabolism.

Glucose-6-phosphate dehydrogenase (G6PDH) catalyzes the first step of the oxidative branch of the pentose phosphate pathway. In this first step, glucose-6-phosphate is oxidized to 6-phosphono-δ-lactone under the action of NADP. This coenzyme is reduced during this oxidation to NADPH2. The reduced form of this coenzyme can catalyze many enzymatic reactions, such as, for example, recycling of glutathione or lipid synthesis. Furthermore, the pentose phosphate pathway produces an essential component for the breakdown of the DNA, the deoxyribose. Reduced glutathione protects many enzymes with the "SH" group and thus promotes the ability of the cell to survive against oxidative stress such as, for example, UV radiation. For said reasons, G6PDH is a very important enzyme for the regeneration of the skin, for the synthesis of essential substances and for the protection of the cells against oxidative stress.

The use of the extracts according to the invention as protecting and restorative care agent is in principle possible for all preparations which are used for the prevention against damage or in cases of damage to the skin and/or hair and thus in skin care and hair care. Another use in this field is the application in cases of sensitive skin damaged by allergy or other causes. The damage to the skin can have a very wide variety of causes.

The preparations according to the invention can be used for the preparation of cosmetic and/or dermopharmaceutical preparations, such as, for example, hair shampoos, hair lotions, foam baths, shower preparations, creams, gels, lotions, alcoholic and aqueous/alcoholic solutions, emulsions, wax/fat compositions, stick preparations, powders or ointments. Furthermore, the preparations according to the invention can, for oral application, also be incorporated into tablets, dragees, capsules, juices, solutions and granules.

These preparations can also comprise, as further auxiliaries and additives, mild surfactants, oily bodies, emulsifiers, pearlescent waxes, bodying agents, thickeners, superfatting agents, stabilizers, polymers, silicone compounds, fats, waxes, lecithins, phospholipids, biogenic active ingredients, UV light protection factors, antioxidants, deodorants, antiperspirants, antidandruff agents, film formers, swelling agents, insect repellents, self-tanning agents, tyrosine inhibitors (depigmentation agents), hydrotropes, solubilizers, preservatives, perfume oils, dyes and the like.

Surfactants

Surface-active substances which may be present are anionic, nonionic, cationic and/or amphoteric or amphoteric surfactants, the content of which in the compositions is usually about 1 to 70% by weight, preferably 5 to 50% by weight and in particular 10 to 30% by weight. Typical examples of anionic surfactants are soaps, alkylbenzenesulfonates, alkanesulfonates, olefin sulfonates, alkyl ether sulfonates, glycerol ether sulfonates, α-methyl ester sulfonates, sulfo fatty acids, alkyl sulfates, fatty alcohol ether sulfates, glycerol ether sulfates, fatty acid ether sulfates, hydroxy mixed ether sulfates, monoglyceride (ether) sulfates, fatty acid amide (ether) sulfates, mono- and dialkyl sulfosuccinates, mono- and dialkyl sulfosuccinamates, sulfotriglycerides, amide soaps, ether carboxylic acids and salts thereof, fatty acid isethionates, fatty acid sarcosinates, fatty acid taurides, N-acylamino acids, such as, for example, acyl lactylates, acyl tartrates, acyl glutamates and acyl aspartates, alkyl oligoglucoside sulfates, protein fatty acid condensates (in particular wheat-based vegetable products) and alkyl (ether) phosphates. If the anionic surfactants contain polyglycol ether chains, these may have a conventional homolog distribution, but preferably have a narrowed homolog distribution. Typical examples of nonionic surfactants are fatty alcohol polyglycol ethers, alkylphenol polyglycol ethers, fatty acid polyglycol esters, fatty acid amide polyglycol ethers, fatty amine polyglycol ethers, alkoxylated triglycerides, mixed ethers or mixed formals, optionally partially oxidized alk(en)yl oligoglycosides or glucoronic acid derivatives, fatty acid N-alkylglucamides, protein hydrolysates (in particular wheat-based vegetable products), polyol fatty acid esters, sugar esters, sorbitan esters, polysorbates and amine oxides. If the nonionic surfactants contain polyglycol ether chains, these may have a conventional homolog distribution, but preferably have a narrowed homolog distribution. Typical examples of cationic surfactants are quaternary ammonium compounds, such as, for example, dimethyl-distearylammonium chloride, and ester quats, in particular quaternized fatty acid trialkanolamine ester salts. Typical examples of amphoteric or zwitterionic surfactants are alkylbetaines, alkylamidobetaines, aminopropionates, aminoglycinates, imidazolinium-betaines and sulfobetaines. Said surfactants are exclusively known compounds. With regard to structure and preparation of these substances, reference may be made to relevant review works, for example, J. Falbe (ed.), "Surfactants in Consumer Products", Springer Verlag, Berlin, 1987, pp. 54-124 or J. Falbe (ed.), "Katalysatoren, Tenside und Mineralöladditive", [catalysts, surfactants and mineral oil additives] Thieme Verlag, Stuttgart, 1978, pp. 123-217. Typical examples of particularly suitable mild, i.e. particularly skin-compatible surfactants are fatty alcohol polyglycol ether sulfates, monoglyceride sulfates, mono- and/or dialkyl sulfosuccinates, fatty acid isethionates, fatty acid sarcosinates, fatty acid taurides, fatty acid glutamates, α-olefinsulfonates, ether carboxylic acids, alkyl oligoglucosides, fatty acid glucamides, alkylamidobetaines, amphoacetals and/or protein fatty acid condensates, the latter preferably based on wheat proteins.

Oily Bodies

Suitable oily bodies are, for example, Guerbet alcohols based on fatty alcohols having 6 to 18, preferably 8 to 10, carbon atoms, esters of linear $C_6$-$C_{22}$-fatty acids with linear or branched $C_6$-$C_{22}$-fatty alcohols or esters of branched $C_6$-$C_{13}$-carboxylic acids with linear or branched $C_6$-$C_{22}$-fatty alcohols, such as, for example, myristyl myristate, myristyl palmitate, myristyl stearate, myristyl isostearate, myristyl oleate, myristyl behenate, myristyl erucate, cetyl myristate, cetyl palmitate, cetyl stearate, cetyl isostearate, cetyl oleate, cetyl behenate, cetyl erucate, stearyl myristate, stearyl palmitate, stearyl stearate, stearyl isostearate, stearyl oleate, stearyl behenate, stearyl erucate, isostearyl myristate, isostearyl palmitate, isostearyl stearate, isostearyl isostearate, isostearyl oleate, isostearyl behenate, isostearyl oleate, oleyl myristate, oleyl palmitate, oleyl stearate, oleyl isostearate, oleyl oleate, oleyl behenate, oleyl erucate, behenyl myristate, behenyl palmitate, behenyl stearate, behenyl isostearate, behenyl oleate, behenyl behenate, behenyl erucate, erucyl myristate, erucyl palmitate, erucyl stearate, erucyl isostearate, erucyl oleate, erucyl behenate and erucyl erucate. Also suitable are esters of linear $C_6$-$C_{22}$-fatty acids with branched alcohols, in particular 2-ethylhexanol, esters of $C_{18}$-$C_{38}$-alkylhydroxycarboxylic acids with linear or branched $C_6$-$C_{22}$-fatty alcohols (cf. DE 19756377 A1), in particular dioctyl malates, esters of linear and/or branched fatty acids with polyhydric alcohols (such as, for example, propylene glycol, dimerdiol or trimertriol) and/or Guerbet alcohols, triglycerides based on $C_6$-$C_{10}$-fatty acids, liquid mono-/di-/triglyceride mixtures based on $C_6$-$C_{18}$-fatty acids, esters of $C_6$-$C_{22}$-fatty alcohols and/or Guerbet alcohols with aromatic carboxylic acids, in particular benzoic acid, esters of $C_2$-$C_{12}$-dicarboxylic acids with linear or branched alcohols having 1 to 22 carbon atoms or polyols having 2 to 10 carbon atoms and 2 to 6 hydroxyl groups, vegetable oils, branched primary alcohols, substituted cyclohexanes, linear and branched $C_6$-$C_{22}$-fatty alcohol carbonates, such as, for example, dicaprylyl carbonates (Cetiol® CC), Guerbet carbonates based on fatty alcohols having 6 to 18, preferably 8 to 10, carbon atoms, esters of benzoic acid with linear and/or branched $C_6$-$C_{22}$-alcohols (e.g. Finsolv® TN), linear or branched, symmetrical or unsymmetrical dialkyl ethers having 6 to 22 carbon atoms per alkyl group, such as, for example, dicaprylyl ether (Cetiol® OE), ring-opening products of epoxidized fatty acid esters with polyols, silicone oils (cyclomethicones, silicon methicone types, inter alia) and/or aliphatic or naphthenic hydrocarbons, such as, for example, such as squalane, squalene or dialkylcyclohexanes.

Emulsifiers

Suitable emulsifiers are, for example, nonionogenic surfactants from at least one of the following groups:

addition products of from 2 to 30 mol of ethylene oxide and/or 0 to 5 mol of propylene oxide onto linear fatty alcohols having 8 to 22 carbon atoms, onto fatty acids having 12 to 22 carbon atoms, onto alkylphenols having 8 to 15 carbon atoms in the alkyl group, and onto alkylamines having 8 to 22 carbon atoms in the alkyl radical;

alkyl and/or alkenyl oligoglycosides having 8 to 22 carbon atoms in the alk(en)yl radical and the ethoxylated analogs thereof;

addition products of from 1 to 15 mol of ethylene oxide to castor oil and/or hydrogenated castor oil;

addition products of from 15 to 60 mol of ethylene oxide to castor oil and/or hydrogenated castor oil;

partial esters of glycerol and/or sorbitan with unsaturated, linear or saturated, branched fatty acids having 12 to 22 carbon atoms and/or hydroxycarboxylic acids having 3 to 18 carbon atoms, and the adducts thereof with 1 to 30 mol of ethylene oxide;

partial esters of polyglycerol (average degree of self-condensation 2 to 8), polyethylene glycol (molecular weight 400 to 5 000), trimethylolpropane, pentaerythritol, sugar alcohols (e.g. sorbitol), alkyl glucosides (e.g. methyl glucoside, butyl glucoside, lauryl glucoside), and polyglucosides (e.g. cellulose) with saturated and/or unsaturated, linear or branched fatty acids having 12 to 22 carbon atoms and/or hydroxycarboxylic acids having 3 to 18 carbon atoms, and the adducts thereof with 1 to 30 mol of ethylene oxide;

mixed esters of pentaerythritol, fatty acids, citric acid and fatty alcohol as in German Patent 1165574 and/or mixed esters of fatty acids having 6 to 22 carbon atoms, methylglucose and polyols, preferably glycerol or polyglycerol, mono-, di- and trialkyl phosphates, and mono-, di- and/or tri-PEG alkyl phosphates and salts thereof;

wool wax alcohols;

polysiloxane-polyalkyl-polyether copolymers and corresponding derivatives;

block copolymers, e.g. polyethylene glycol-30 dipolyhydroxystearates;

polymer emulsifiers, e.g. Pemulen grades (TR-1, TR-2) from Goodrich;

polyalkylene glycols, and glycerol carbonate.

The addition products of ethylene oxide and/or propylene oxide onto fatty alcohols, fatty acids, alkylphenols or onto castor oil are known, commercially available products. These are homolog mixtures whose average degree of alkoxylation corresponds to the ratio of the amounts of ethylene oxide and/or propylene oxide and substrate with which the addition reaction is carried out. $C_{12/18}$-fatty acid mono- and diesters of addition products of ethylene oxide onto glycerol are known from German Patent 2024051 as refatting agents for cosmetic preparations.

Alkyl and/or alkenyl oligoglycosides, their preparation and their use are known from the prior art. They are prepared, in particular, by reacting glucose or oligo-saccharides with primary alcohols having 8 to 18 carbon atoms. With regard to the glycoside radical, both monoglycosides, in which a cyclic sugar radical is glycosidically bonded to the fatty alcohol, and also oligomeric glycosides having a degree of oligomerization of up to, preferably, about 8, are suitable. The degree of oligomerization here is a statistical average value which is based on a homolog distribution customary for such technical-grade products.

Typical examples of suitable partial glycerides are hydroxystearic acid monoglyceride, hydroxystearic acid diglyceride, isostearic acid monoglyceride, isostearic acid diglyceride, oleic acid monoglyceride, oleic acid diglyceride, ricinoleic acid moglyceride, ricinoleic acid diglyceride, linoleic acid monoglyceride, linoleic acid diglyceride, linolenic acid monoglyceride, linolenic acid diglyceride, erucic acid monoglyceride, erucic acid diglyceride, tartaric acid monoglyceride, tartaric acid diglyceride, citric acid monoglyceride, citric acid diglyceride, malic acid monoglyceride, malic acid diglyceride, and the technical-grade mixtures thereof which may also comprise small amounts of triglyceride as a minor product of the preparation process. Likewise suitable are addition products of 1 to 30 mol, preferably 5 to 10 mol, of ethylene oxide to said partial glycerides.

Suitable sorbitan esters are sorbitan monoisostearate, sorbitan sesquiisostearate, sorbitan diisostearate, sorbitan triisostearate, sorbitan monooleate, sorbitan sesquioleate, sorbitan dioleate, sorbitan trioleate, sorbitan monoerucate, sorbitan sesquierucate, sorbitan dierucate, sorbitan trierucate, sorbitan monoricinoleate, sorbitan sesquiricinoleate, sorbitan diricinoleate, sorbitan triricinoleate, sorbitan monohydroxystearate, sorbitan sesquihydroxystearate, sorbitan dihydroxystearate, sorbitan trihydroxystearate, sorbitan monotartrate, sorbitan sesquitartrate, sorbitan ditartrate, sorbitan tritartrate, sorbitan monocitrate, sorbitan sesquicitrate, sorbitan dicitrate, sorbitan tricitrate, sorbitan monomaleate, sorbitan sesquimaleate, sorbitan dimaleate, sorbitan trimaleate, and technical-grade mixtures thereof. Likewise suitable are addition products of 1 to 30 mol, preferably 5 to 10 mol, of ethylene oxide to said sorbitan esters.

Typical examples of suitable polyglycerol esters are polyglyceryl-2 dipolyhydroxystearate (Dehymuls® PGPH), polyglycerol-3 diisostearate (Lameform® TGI), polyglyceryl-4 isostearate (Isolan® GI 34), polyglyceryl-3 oleate, diisostearoyl polyglyceryl-3 diisostearate (Isolan® PDI), polyglyceryl-3 methylglucose distearate (Tego Care® 450), polyglyceryl-3 beeswax (Cera Bellina®), polyglyceryl-4 caprate (Polyglycerol Caprate T2010/90), polyglyceryl-3 cetyl ether (Chimexane® NL), polyglyceryl-3 distearate (Cremophor® GS 32) and polyglyceryl polyricinoleate (Admul® WOL 1403), polyglyceryl dimerate isostearate, and mixtures thereof. Examples of further suitable polyol esters are the mono-, di- and triesters, optionally reacted with 1 to 30 mol of ethylene oxide, of trimethylolpropane or pentaerythritol with lauric acid, coconut fatty acid, tallow fatty acid, palmitic acid, stearic acid, oleic acid, behenic acid and the like.

Furthermore, zwitterionic surfactants can be used as emulsifiers. The term "zwitterionic surfactants" refers to those surface-active compounds which carry at least one quaternary ammonium group and at least one carboxylate and one sulfonate group in the molecule. Particularly suitable zwitterionic surfactants are the betaines, such as N-alkyl-N,N-dimethylammonium glycinates, for example cocoalkyldimethylammonium glycinate, N-acylaminopropyl-N,N-dimethylammonium glycinates, for example cocoacylaminopropyldimethylammonium glycinate, and 2-alkyl-3-carboxymethyl-3-hydroxyethylimidazolines having in each case 8 to 18 carbon atoms in the alkyl or acyl group, and cocoacylaminoethylhydroxyethyl-carboxymethyl glycinate. Particular preference is given to the fatty acid amide derivative known under the CTFA name Cocamidopropyl Betaine. Likewise suitable emulsifiers are ampholytic surfactants. The term "ampholytic surfactants" means those surface-active compounds which, apart from a $C_{8/18}$-alkyl or -acyl group in the molecule, contain at least one free amino group and at least one —COOH or —SO$_3$H group and are capable of forming internal salts. Examples of suitable ampholytic surfactants are N-alkylglycines, N-alkylpropionic acids, N-alkylaminobutyric acids, N-alkyliminodipropionic acids, N-hydroxyethyl-N-alkylamidopropylglycines, N-alkyltaurines, N-alkylsarcosines, 2-alkylaminopropionic acids and alkylaminoacetic acids having in each case about 8 to 18 carbon atoms in the alkyl group. Particularly preferred ampholytic surfactants are N-cocoalkyl aminopropionate, cocoacylaminoethyl aminopropionate and $C_{12/18}$-acylsarcosine. Finally, cationic surfactants are also suitable emulsifiers, those of the ester quat type, preferably methyl-quaternized difatty acid triethanolamine ester salts, being particularly preferred.

Fats and Waxes

Typical examples of fats are glycerides, i.e. solid or liquid vegetable or animal products which consist essentially of mixed glycerol esters of higher fatty acids, suitable waxes are inter alia natural waxes, such as, for example, candelilla wax, carnauba wax, japan wax, esparto grass wax, cork wax, guaruma wax, rice germ oil wax, sugarcane wax, ouricury wax, montan wax, beeswax, shellac wax, spermaceti, lanolin (wool wax), uropygial grease, ceresin, ozokerite (earth wax), petrolatum, paraffin waxes, microcrystalline waxes; chemically modified waxes (hard waxes), such as, for example, montan ester waxes, sasol waxes, hydrogenated jojoba waxes, and synthetic waxes, such as, for example, polyalkylene waxes and polyethylene glycol waxes. In addition to the fats, suitable additives are also fat-like substances, such as lecithins and phospholipids. The term lecithins is understood by the person skilled in the art as meaning those glycerophospholipids which form from fatty acids, glycerol, phosphoric acid and choline by esterification. Lecithins are thus frequently also known as phosphatidylcholines (PC). Examples of natural lecithins which may be mentioned are the cephalins, which are also referred to as phosphatidic acids and represent derivatives of 1,2-diacyl-sn-glycerol-3-phosphoric acids. By contrast, phospholipids are usually understood as meaning mono- and, preferably, diesters of phosphoric acid with glycerol (glycerophosphates), which are generally considered to be fats. In addition, sphingosines and sphingolipids are also suitable.

Pearlescent Waxes

Examples of suitable pearlescent waxes are: alkylene glycol esters, specifically ethylene glycol distearate; fatty acid alkanolamides, specifically coconut fatty acid diethanolamide; partial glycerides, specifically stearic acid monoglyceride; esters of polybasic, optionally hydroxy-substituted carboxylic acids with fatty alcohols having 6 to 22 carbon atoms, specifically long-chain esters of tartaric acid; fatty substances, such as, for example, fatty alcohols, fatty ketones, fatty aldehydes, fatty ethers and fatty carbonates, which have a total of at least 24 carbon atoms, specifically laurone and distearyl ether; fatty acids, such as stearic acid, hydroxystearic acid or behenic acid, ring-opening products of olefin epoxides having 12 to 22 carbon atoms with fatty alcohols having 12 to 22 carbon atoms and/or polyols having 2 to 15 carbon atoms and 2 to 10 hydroxyl groups, and mixtures thereof.

Bodying Agents and Thickeners

Suitable bodying agents are primarily fatty alcohols or hydroxy fatty alcohols having 12 to 22, and preferably 16 to 18, carbon atoms, and also partial glycerides, fatty acids or hydroxy fatty acids. Preference is given to a combination of these substances with alkyl oligo-glucosides and/or fatty acid N-methylglucamides of identical chain length and/or polyglycerol poly-12-hydroxystearates. Suitable thickeners are, for example, Aerosil grades (hydrophilic silicas), polysaccharides, in particular xanthan gum, guar guar, agar agar, alginates and Tyloses, carboxymethylcellulose and hydroxyethylcellulose, and also relatively high molecular weight polyethylene glycol mono- and diesters of fatty acids, polyacrylates (e.g. Carbopols and Pemulen grades from Goodrich; Synthalens® from Sigma; Keltrol grades from Kelco; Sepigel grades from Seppic; Salcare grades from Allied Colloids), polyacrylamides, polymers, polyvinyl alcohol and polyvinylpyrrolidone, surfactants, such as, for example, ethoxylated fatty acid glycerides, esters of fatty acids with polyols such as, for example, pentaerythritol or trimethylolpropane, fatty alcohol ethoxylates having a narrowed homolog distribution or alkyl oligoglucosides, and electrolytes such as sodium chloride and ammonium chloride.

Superfatting Agents

Superfatting agents which can be used are substances such as, for example, lanolin and lecithin, and poly-ethoxylated or acylated lanolin and lecithin derivatives, polyol fatty acid esters, monoglycerides and fatty acid alkanolamides, the latter also serving as foam stabilizers.

Stabilizers

Stabilizers which can be used are metal salts of fatty acids, such as, for example, magnesium, aluminum and/or zinc stearate or ricinoleate.

Polymers

Suitable cationic polymers are, for example, cationic cellulose derivatives, such as, for example, a quaternized hydroxyethylcellulose obtainable under the name Polymer JR 400® from Amerchol, cationic starch, copolymers of diallylammonium salts and acrylamides, quaternized vinylpyrrolidone-vinylimidazole polymers, such as, for example, Luviquat® (BASF), condensation products of polyglycols and amines, quaternized collagen polypeptides, such as, for example, lauryldimonium hydroxypropyl hydrolyzed collagen (Lamequat® L/Grünau), quaternized wheat polypeptides, polyethyleneimine, cationic silicone polymers, such as, for example, amodimethicones, copolymers of adipic acid and dimethyl-aminohydroxypropyldiethylenetriamine (Cartaretins®/Sandoz), copolymers of acrylic acid with dimethyldiallylammonium chloride (Merquat® 550/Chemviron), polyaminopolyamides, as described, for example, in FR 2252840 A, and crosslinked water-soluble polymers thereof, cationic chitin derivatives, such as, for example, quaternized chitosan, optionally in micro-crystalline dispersion, condensation products from dihaloalkyls, such as, for example, dibromobutane with bisdialkylamines, such as, for example, bis-dimethyl-amino-1,3-propane, cationic guar gum, such as, for example, Jaguar® CBS, Jaguar® C-17, Jaguar® C-16 from Celanese, quaternized ammonium salt polymers, such as, for example, Mirapol® A-15, Mirapol® AD-1, Mirapol® AZ-1 from Miranol.

Suitable anionic, zwitterionic, amphoteric and nonionic polymers are, for example, vinyl acetate-crotonic acid copolymers, vinylpyrrolidone-vinyl acrylate copolymers, vinyl acetate-butyl maleate-isobornyl acrylate copolymers, methyl vinyl ether-maleic anhydride copolymers and esters thereof, uncrosslinked polyacrylic acids and polyacrylic acids crosslinked with polyols, acrylamido-propyltrimethylammonium chloride-acrylate copolymers, octylacrylamide-methyl methacrylate-tert-butylaminoethyl methacrylate-2-hydroxypropyl methacrylate copolymers, polyvinylpyrrolidone, vinylpyrrolidone-vinyl acetate copolymers, vinylpyrrolidone-dimethylaminoethyl methacrylate-vinylcaprolactam terpolymers, and optionally derivatized cellulose ethers and silicones. Further suitable polymers and thickeners are listed in Cosm. Toil. 108, 95 (1993).

Silicone Compounds

Suitable silicone compounds are, for example, dimethylpolysiloxanes, methylphenylpolysiloxanes, cyclic silicones, and amino-, fatty-acid-, alcohol-, polyether-, epoxy-, fluorine-, glycoside- and/or alkyl-modified silicone compounds, which can either be liquid or in resin form at room temperature. Also suitable are simethicones, which are mixtures of dimethicones having an average chain length of from 200 to 300 dimethyl-siloxane units and hydrogenated silicates. A detailed review of suitable volatile silicones can additionally be found in Todd et al., Cosm. Toil. 91, 27 (1976).

Antioxidants

As well as said groups of primary light protection substances, it is also possible to use secondary light protection agents of the antioxidant type which interrupt the photochemical reaction chain which is triggered when UV radiation penetrates into the skin. Typical examples thereof are amino acids (e.g. glycine, histidine, tyrosine, tryptophan) and derivatives thereof, imidazoles (e.g. urocanic acid) and derivatives thereof, peptides, such as D,L-carnosine, D-carnosine, L-carnosine and derivatives thereof (e.g. anserine), carotenoids, carotenes (e.g. α-carotene, β-carotene, lycopene) and derivatives thereof, chlorogenic acid and derivatives thereof, lipoic acid and derivatives thereof (e.g. dihydrolipoic acid), aurothioglucose, propylthiouracil and other thiols (e.g. thioredoxin, glutathione, cysteine, cystine, cystamine and the glycosyl, N-acetyl, methyl, ethyl, propyl, amyl, butyl and lauryl, palmitoyl, oleyl, γ-linoleyl, cholesteryl and glyceryl esters thereof) and salts thereof, dilauryl thiodipropionate, distearyl thiodipropionate, thiodipropionic acid and derivatives thereof (esters, ethers, peptides, lipids, nucleotides, nucleosides and salts), and sulfoximine compounds (e.g. buthionine sulfoximines, homocysteine sulfoximine, buthionine sulfones, penta-, hexa-, heptathionine sulfoximine) in very low tolerated doses (e.g. pmol to μmol/kg), and also (metal) chelating agents (e.g. α-hydroxy fatty acids, palmitic acid, phytic acid, lactoferrin), α-hydroxy acids (e.g. citric acid, lactic acid, malic acid), humic acid, bile acid, bile extracts, bilirubin, biliverdin, EDTA, EGTA and derivatives thereof, unsaturated fatty acids and derivatives thereof (e.g.

γ-linolenic acid, linoleic acid, oleic acid), folic acid and derivatives thereof, ubiquinone and ubiquinol and derivatives thereof, vitamin C and derivatives (e.g. ascorbyl palmitate, Mg ascorbyl phosphate, ascorbyl acetate), tocopherols and derivatives (e.g. vitamin E acetate), vitamin A and derivatives (vitamin A palmitate), and coniferyl benzoate of gum benzoin, rutic acid and derivatives thereof, α-glycosylrutin, ferulic acid, furfurylideneglucitol, carnosine, butyl-hydroxytoluene, butylhydroxyanisole, nordihydroguaiacic acid, nordihydroguaiaretic acid, trihydroxybutyrophenone, uric acid and derivatives thereof, mannose and derivatives thereof, superoxide dismutase, zinc and derivatives thereof (e.g. ZnO, $ZnSO_4$) selenium and derivatives thereof (e.g. selenomethionine), stilbenes and derivatives thereof (e.g. stilbene oxide, trans-stilbene oxide) and the derivatives (salts, esters, ethers, sugars, nucleotides, nucleosides, peptides and lipids) of said active ingredients which are suitable according to the invention.

Biogenic Active Ingredients

Within the scope of the invention, biogenic active ingredients are additionally understood as meaning those which do not arise from the plant *Argania spinosa*, such as, for example, tocopherol acetate, tocopherol palmitate, ascorbic acid, (deoxy)ribonucleic acid and fragmentation products thereof, retinol, bisabolol, allantoin, phytantriol, panthenol, AHA acids, amino acids, ceramides, pseudoceramides, essential oils, further plant extracts and additional vitamin complexes.

Deodorants and Antimicrobial Agents

Cosmetic deodorants counteract, mask or remove body odors. Body odors arise as a result of the effect of skin bacteria on apocrine perspiration, with the formation of degradation products which have an unpleasant odor. Accordingly, deodorants comprise active ingredients which act as antimicrobial agents, enzyme inhibitors, odor absorbers or odor masking agents. Suitable antimicrobial agents are, in principle, all substances effective against gram-positive bacteria, such as, for example, 4-hydroxybenzoic acid and its salts and esters, N-(4-chlorophenyl)-N'-(3,4-dichlorophenyl) urea, 2,4,4'-trichloro-2'-hydroxydiphenyl ether (triclosan), 4-chloro-3,5-dimethylphenol, 2,2'-methylenebis(6-bromo-4-chlorophenol), 3-methyl-4-(1-methylethyl)phenol, 2-benzyl-4-chlorophenol, 3-(4-chlorophenoxy)-1,2-propanediol, 3-iodo-2-propynyl butylcarbamate, chlorohexidine, 3,4,4'-trichlorocarbanilide (TTC), antibacterial fragrances, thymol, thyme oil, eugenol, oil of cloves, menthol, mint oil, farnesol, phenoxyethanol, glycerol monocaprate, glycerol monocaprylate, glycerol monolaurate (GML), diglycerol monocaprate (DMC), salicylic acid N-alkylamides, such as, for example, n-octylsalicylamide or n-decylsalicylamide.

Suitable enzyme inhibitors are, for example, esterase inhibitors. These are preferably trialkyl citrates, such as trimethyl citrate, tripropyl citrate, triisopropyl citrate, tributyl citrate and, in particular, triethyl citrate (Hydagen® CAT). The substances inhibit enzyme activity, thereby reducing the formation of odor. Other substances which are suitable esterase inhibitors are sterol sulfates or phosphates, such as, for example, lanosterol, cholesterol, campesterol, stigmasterol and sitosterol sulfate or phosphate, dicarboxylic acids and esters thereof, such as, for example, glutaric acid, monoethyl glutarate, diethyl glutarate, adipic acid, monoethyl adipate, diethyl adipate, malonic acid and diethyl malonate, hydroxycarboxylic acids and esters thereof, such as, for example, citric acid, malic acid, tartaric acid or diethyl tartrate, and zinc glycinate.

Suitable odor absorbers are substances which are able to absorb and largely retain odor-forming compounds. They lower the partial pressure of the individual components, thus also reducing their rate of diffusion. It is important that in this process perfumes must remain unimpaired. Odor absorbers are not effective against bacteria. They comprise, for example, as main constituent, a complex zinc salt of ricinoleic acid or specific, largely odor-neutral fragrances which are known to the person skilled in the art as "fixatives", such as, for example, extracts of labdanum or styrax or certain abietic acid derivatives. The odor masking agents are fragrances or perfume oils, which, in addition to their function as odor masking agents, give the deodorants their respective fragrance note. Perfume oils which may be mentioned are, for example, mixtures of natural and synthetic fragrances. Natural fragrances are extracts from flowers, stems and leaves, fruits, fruit peels, roots, woods, herbs and grasses, needles and branches, and resins and balsams. Also suitable are animal raw materials, such as, for example, civet and castoreum. Typical synthetic fragrance compounds are products of the ester, ether, aldehyde, ketone, alcohol and hydrocarbon type. Fragrance compounds of the ester type are, for example, benzyl acetate, p-tert-butylcyclohexyl acetate, linalyl acetate, phenylethyl acetate, linalyl benzoate, benzyl formate, allyl cyclohexylpropionate, styrallyl propionate and benzyl salicylate. The ethers include, for example, benzyl ethyl ether, and the aldehydes include, for example, the linear alkanals having 8 to 18 carbon atoms, citral, citronellal, citronellyloxyacetaldehyde, cyclamen aldehyde, hydroxycitronellal, lilial and bourgeonal, the ketones include, for example, the ionones and methyl cedryl ketone, the alcohols include anethol, citronellol, eugenol, isoeugenol, geraniol, linalool, phenylethyl alcohol and terpineol, and the hydrocarbons include mainly the terpenes and balsams. Preference is, however, given to using mixtures of different fragrances which together produce a pleasing fragrance note. Ethereal oils of relatively low volatility, which are mostly used as aroma components, are also suitable as perfume oils, e.g. sage oil, camomile oil, oil of cloves, melissa oil, mint oil, cinnamon leaf oil, linden flower oil, juniper berry oil, vetiver oil, olibanum oil, galbanum oil, labdanum oil and lavandin oil. Preference is given to using bergamot oil, dihydromyrcenol, lilial, lyral, citronellol, phenylethyl alcohol, α-hexylcinnamaldehyde, geraniol, benzylacetone, cyclamenaldehyde, linalool, boisambrene forte, ambroxan, indole, hedione, sandelice, lemon oil, mandarin oil, orange oil, allyl amyl glycolate, cyclovertal, lavandin oil, clary sage oil, β-damascone, geranium oil bourbon, cyclohexyl salicylate, Vertofix coeur, iso-E-super, Fixolide NP, evernyl, iraldein gamma, phenylacetic acid, geranyl acetate, benzyl acetate, rose oxide, romilat, irotyl and floramat alone or in mixtures.

Antiperspirants reduce the formation of perspiration by influencing the activity of the eccrine sweat glands, thus counteracting underarm wetness and body odor. Aqueous or anhydrous formulations of antiperspirants typically comprise the following ingredients:
  astringent active ingredients,
  oil components,
  nonionic emulsifiers,
  coemulsifiers,
  bodying agents,
  auxiliaries, such as, for example, thickeners or complexing agents and/or
  nonaqueous solvents, such as, for example, ethanol, propylene glycol and/or glycerol.

Suitable astringent antiperspirant active ingredients are primarily salts of aluminum, zirconium or of zinc. Such suitable antihydrotic active ingredients are, for example, aluminum chloride, aluminum chlorohydrate, aluminum dichlorohydrate, aluminum sesquichlorohydrate and complex compounds thereof, e.g. with 1,2-propylene glycol, aluminum hydroxyallantoinate, aluminum chloride tartrate, aluminum zirconium trichlorohydrate, aluminum zirconium tetrachlorohydrate, aluminum zirconium penta-chlorohydrate and complex compounds thereof, e.g. with amino acids, such as glycine. In addition, customary oil-soluble and water-soluble auxiliaries may be present in antiperspirants in relatively small amounts. Such oil-soluble auxiliaries may, for example, be:

- anti-inflammatory, skin-protective or perfumed ethereal oils,
- synthetic skin-protective active ingredients and/or oil-soluble perfume oils.

Customary water-soluble additives are, for example, preservatives, water-soluble fragrances, pH regulators, e.g. buffer mixtures, water-soluble thickeners, e.g. water-soluble natural or synthetic polymers, such as, for example, xanthan gum, hydroxyethylcellulose, polyvinylpyrrolidone or high molecular weight polyethylene oxides.

Film Formers

Customary film formers are, for example, chitosan, microcrystalline chitosan, quaternized chitosan, polyvinylpyrrolidone, vinylpyrrolidone-vinyl acetate copolymers, polymers of the acrylic acid series, quaternary cellulose derivatives, collagen, hyaluronic acid and salts thereof, and similar compounds.

Antidandruff Active Ingredients

Suitable antidandruff active ingredients are piroctone olamine (1-hydroxy-4-methyl-6-(2,4,4-trimethylpentyl)-2-(1H)-pyridinone monoethanolamine salt), Baypival® (climbazole), Ketoconazole®, (4-acetyl-1-{-4-[2-(2,4-dichlorophenyl)]-2-(1H-imidazol-1-ylmethyl)-1,3-dioxylan-c-4-ylmethoxyphenyl}piperazine, ketoconazole, elubiol, selenium disulfide, colloidal sulfur, sulfur polyethylene glycol sorbitan monooleate, sulfur ricinol polyethoxylate, sulfur tar distillates, salicylic acid (or in combination with hexachlorophene), undecylenic acid monoethanolamide sulfosuccinate Na salt, Lamepon® UD (protein undecylenic acid condensate), zinc pyrithione, aluminum pyrithione and magnesium pyrithione/dipyrithione magnesium sulfate.

Swelling Agents

The swelling agents for aqueous phases may be montmorillonites, clay mineral substances, Pemulen, and alkyl-modified Carbopol grades (Goodrich). Other suitable polymers and swelling agents are given in the review by R. Lochhead in Cosm. Toil. 108, 95 (1993).

Insect Repellents

Suitable insect repellents are N,N-diethyl-m-toluamide, 1,2-pentanediol or ethyl butylacetylaminopropionate.

Self-Tanning Agents and Depigmentation Agents

A suitable self-tanning agent is dihydroxyacetone. Suitable tyrosine inhibitors, which prevent the formation of melanin and are used in depigmentation agents are, for example, arbutin, ferulic acid, kojic acid, coumaric acid and ascorbic acid (vitamin C).

Hydrotropes

To improve the flow behavior, hydrotropes, such as, for example, ethanol, isopropyl alcohol, or polyols, can also be used. Polyols which are suitable here preferably have 2 to 15 carbon atoms and at least two hydroxyl groups. The polyols can also contain further functional groups, in particular amino groups, or be modified with nitrogen. Typical examples are

- glycerol;
- alkylene glycols, such as, for example, ethylene glycol, diethylene glycol, propylene glycol, butylene glycol, hexylene glycol, and polyethylene glycols with an average molecular weight of from 100 to 1 000 daltons;
- technical-grade oligoglycerol mixtures with a degree of self-condensation of from 1.5 to 10, such as, for example, technical-grade diglycerol mixtures with a diglycerol content of from 40 to 50% by weight;
- methylol compounds, such as, in particular, trimethylolethane, trimethylolpropane, trimethylolbutane, pentaerythritol and dipentaerythritol;
- lower alkyl glucosides, in particular those with 1 to 8 carbon atoms in the alkyl radical, such as, for example, methyl and butyl glucoside;
- sugar alcohols with 5 to 12 carbon atoms, such as, for example, sorbitol or mannitol,
- sugars with 5 to 12 carbon atoms, such as, for example, glucose or sucrose;
- amino sugars, such as, for example, glucamine;
- dialcohol amines, such as diethanolamine or 2-amino-1,3-propanediol.

Preservatives

Suitable preservatives are, for example, phenoxyethanol, formaldehyde solution, parabenes, pentanediol or sorbic acid, and the other classes of substance listed in Annex 6, Part A and B of the Cosmetics Directive.

Perfume Oils

Perfume oils which may be mentioned are mixtures of natural and synthetic fragrances. Natural fragrances are extracts from flowers (lily, lavender, rose, jasmine, neroli, ylang-ylang), stems and leaves (geranium, patchouli, petitgrain), fruits (aniseed, coriander, cumin, juniper), fruit peels (bergamot, lemon, orange), roots (mace, angelica, celery, cardamom, costus, iris, calmus), woods (pine wood, sandalwood, guaiac wood, cedarwood, rosewood), herbs and grasses (tarragon, lemon grass, sage, thyme), needles and branches (spruce, fir, pine, dwarf-pine), resins and balsams (galbanum, elemi, benzoin, myrrh, olibanum, opoponax). Also suitable are animal raw materials, such as, for example, civet and castoreum. Typical synthetic fragrance compounds are products of the ester, ether, aldehyde, ketone, alcohol and hydrocarbon type. Fragrance compounds of the ester type are, for example, benzyl acetate, phenoxyethyl isobutyrate, p-tert-butylcyclohexyl acetate, linalyl acetate, dimethylbenzylcarbinyl acetate, phenylethyl acetate, linalyl benzoate, benzyl formate, ethylmethylphenyl glycinate, allyl cyclohexylpropionate, styrallyl propionate and benzyl salicylate. The ethers include, for example, benzyl ethyl ether, the aldehydes include, for example, the linear alkanals having 8 to 18 carbon atoms, citral, citronellal, citronellyloxyacetaldehyde, cyclamen aldehyde, hydroxycitronellal, lilial and bourgeonal, and the ketones include, for example, the ionones, α-isomethylionone and methyl cedryl ketone, the alcohols include anethole, citronellol, eugenol, isoeugenol, geraniol, linalool, phenylethyl alcohol and terpineol, and the hydrocarbons include predominantly the terpenes and balsams. Preference is, however, given to using mixtures of different fragrances which together produce a pleasing fragrance note. Ethereal oils of relatively low volatility, which are mostly used as aroma components, are also suitable as perfume oils, e.g. sage oil, camomile oil, oil of cloves, melissa oil, mint oil, cinnamon leaf oil, linden blossom oil, juniper berry oil, vetiver oil, olibanum oil, galbanum oil, labolanum oil and lavandin oil.

Preference is given to using bergamot oil, dihydromyrcenol, lilial, lyral, citronellol, phenylethyl alcohol, α-hexylcinnamaldehyde, geraniol, benzylacetone, cyclamenaldehyde, linalool, boisambrene forte, ambroxan, indole, hedione, sandelice, lemon oil, mandarin oil, orange oil, allyl amyl glycolate, cyclovertal, lavandin oil, clary sage oil, β-damascone, geranium oil bourbon, cyclohexyl salicylate, Vertofix coeur, iso-E-super, Fixolide NP, evernyl, iraldein gamma, phenylacetic acid, geranyl acetate, benzyl acetate, rose oxide, romilat, irotyl and floramat alone or in mixtures.

Dyes

Dyes which can be used are the substances which are approved and suitable for cosmetic purposes, as are summarized, for example, in the publication "Kosmetische Färbemittel" [Cosmetic Colorants] from the Farbstoffkommission der Deutschen Forschungsgemeinschaft [Dyes Commission of the German Research Council], Verlag Chemie, Weinheim, 1984, pp. 81-106. These dyes are normally used in concentrations of from 0.001 to 0.1% by weight, based on the total mixture.

EXAMPLES

1. Example

Extraction of the Plants with Distilled Water 0.2 kg of defatted *Argania spinosa* seeds obtained from the residue of the extraction for oil production were transferred to a glass vessel and 2 l of distilled water were poured onto them. The mixture was stirred for two hours at room temperature. The pH of the solution was between 6.2 and 6.0. The mixture was then centrifuged for 15 minutes at a speed of 5000 g. The supernatant liquid was separated from the residue by filtration over a deep-bed filter with an average porosity of 450 nm (from Seitz, Bordeaux, France). The yield of native proteins, calculated on the basis of the dry weight (according to N×6.25), was 35 to 55% by weight.

2. Example

Work-Up of the Extract by Thermocleaning

Example 1 was repeated, but the purification was carried out by the thermocleaning process. For this, the supernatant liquid, following the centrifugation described as under example 1, was heated at 80-100° C. for 30 min, which led to precipitation of the thermally unstable native proteins, and then cooled to room temperature. The mixture was then centrifuged at a speed of 5000 g for 15 min and separated from the residue by filtration over a deep-bed filter with an average porosity of 220 nm (from Seitz, Bordeaux, France).

By means of chromatography over Superose 12HR, it was possible to isolate three main fractions of native proteins. These had molecular weights in the following ranges:

TABLE 1

Molecular weight ranges of the extracted native proteins

| | Molecular weight range (Da) | Amount (% by wt.) |
|---|---|---|
| Fraction 1 | greater than/equal to 500 000 | 16 |
| Fraction 2 | 187 000 to 210 000 | 55 |
| Fraction 3 | 13 000 to 16 000 | 14 |

3. Example

Extraction with Concentration of Fraction 2

Example 1 was repeated as far as the centrifugation. 1.6 liters of this protein extract were placed into a reactor and adjusted to a pH of 4.5 with stirring by adding 4 N sulfuric acid. This mixture was stirred for 15 to 30 min. The mixture was then centrifuged at a speed of 5000 g for 15 min. The resulting residue was enriched with the fraction in the molecular weight range between 187 000 and 210 000 Da, in particular with proteins with a molecular weight of 200 000 Da, and the supernatant comprised the protein fraction with the lowest molecular weight. The residue was taken up in 160 ml of water and the pH was adjusted to pH 6.1 with stirring by adding 4 N NaOH. The resulting solution was again centrifuged under the conditions described and dried by freeze drying. As a result of this concentration, it was possible to obtain an extract which comprised 70-85% by weight of the native proteins according to fraction 2 from example 2. The overall protein content in the resulting dried extract was 60-85% by weight by this extraction method.

4. Example

Extraction with Concentration of Fraction 3

1.48 liters of the residue from example 3 were separated from the residue by filtration over a deep-bed filter with an average porosity of 220 nm (from Seitz, Bordeaux, France) and then freeze-dried. As a result of this enrichment, it was possible to obtain an extract which comprised 21-40% by weight of the native proteins according to fraction 3 from example 2. The overall protein content in the resulting dried extract was 40-50% by weight by this extraction method, shown by a UV chromatogram.

5. Example

Test to Regulate Moisture in the Skin

Background: In the epidermis of human skin there is the horny layer (the Stratum corneum), its water content guarantees it on the one hand its elasticity and determines on the other hand the amount and possibly also the size of the peeled-off horny scales, which are themselves microscopically small.

Method: Samples from plastic surgery were used for this moisture-regulating test. Two different conditions were tested. Firstly, normal skin was investigated as the control, and secondly a skin sample whose surface was damaged was treated and investigated. The Stratum corneum from these skin samples was immersed for one hour in a 5% strength solution of sodium lauryl sulfate, then dried at room temperature and, mounted on grids, stored and standardized in hermetically sealed chambers with a defined relative humidity (44%, saturated solution of potassium carbonate). Each sample of the Stratum corneum was tested for comparison purposes under three conditions.

1) without treatment;
2) treatment with placebo;
3) treatment with a preparation which consists of a binder (Hydrogel LS from Laboratoire Sérobiologique LS), comprising 5% by weight of extract as in example 4.

In each case 2 mg/cm$^2$ of placebo or preparation as in 3) were applied to the external surface. The placebo used was the binder (Hydrogel LS from Laboratoire Sérobiologique LS) without the described preparation, i.e. without plant extract.

The moisture-regulating activity of the native proteins according to the invention in the preparation described above were determined through the loss of moisture in the Stratum corneum over a period of 24 hours, given in mg/h/cm$^2$ compared to the placebo treatment.

TABLE 2

Moisture-regulating effect, determined by measuring the moisture loss (in mg/h/cm$^2$), brackets give the standard deviation

| Stratum corneum | Control without treatment | Treatment with placebo | Treatment as in 3) |
|---|---|---|---|
| Control (skin without damage) | 0.34 (0.06) | 0.34 (0.02) | 0.31 (0.02) |
| Damaged skin | 0.62 (0.14) | 0.62 (0.13) | 0.53 (0.12) |

The results of the investigation show a moisture-regulating activity of the native proteins from *Argania spinosa*. The skin samples which were treated as in 3) exhibited a significantly lower loss of moisture over the course of 24 hours than untreated skin samples. The difference was even more marked in the case of skin which was already damaged than in the case of skin without damage.

6. Skin-Smoothing Effects

Dynamic Spring Rate

Background: The principle of this method consists in determining a shift or displacement of the skin in response to a small sinusoidal force which is applied in parallel to the surface of the skin. This force is generated using a gas-bearing electrodynamometer. The parameter investigated is the "dynamic spring rate" (DSR) which expresses the relationship of applied force to shift of the skin. The greater the shift of the skin relative to the applied force, the more supple the skin, and vice versa.

A high shiftability of the skin following treatment with the samples to be investigated is expressed by a reduction in the DSR, and an increase in the dynamic spring rate shows a smoothing, stabilizing action of the sample to be investigated on the skin.

Method: The skin sample was mounted and attached to a microscope slide. The attached skin was equilibrated over two hours in an atmosphere with controlled atmospheric humidity (33%) and a constant temperature (T=20° C.). The mechanical properties were then determined for comparison purposes under three conditions. The results are shown as development of the DSR after 90 minutes.

TABLE 3

Skin-smoothing and stabilizing effect, determined by measuring the dynamic spring rate (DSR) which expresses the relationship of applied force to shift of the skin

| | DSR after 90 min |
|---|---|
| Control without treatment | 98% |
| Placebo hydrogel without Argania spinosa extract | 116% |
| Hydrogel comprising 2% by weight of extract as in example 3 | 135% |

TABLE 3-continued

Skin-smoothing and stabilizing effect, determined by measuring the dynamic spring rate (DSR) which expresses the relationship of applied force to shift of the skin

| | DSR after 90 min |
|---|---|
| Hydrogel comprising 6% by weight of extract as in example 4 | 142% |

In each case 4 mg/cm$^2$ of hydrogel were applied.

Compared to the placebo and control experiments, the increase in the DSR value for hydrogel comprising extracts of *Argania spinosa* was significant. These increased values show that for a shift of the attached skin following treatment with the samples to be investigated, a greater force must be applied than without extract from *Argania spinosa*, and these values thus show a smoothing and stabilizing action of the extracts according to the invention on the skin.

7. Effect on the Survival Activity of Human Fibroblasts

To assess cell activity, there are fundamental markers, which include MTT, proteins and glutathione.

The survival was evaluated by means of the following contents:

Rate of the metabolized MTT (Methyl Thiazolyl Tetrazolium); the mitochondrial activity is determined by means of the MTT test. MTT is reduced by an enzyme of the respiration chain, succinate dehydrogenase, into formazan (Denizot F, Lang R, Rapid colorimetric assay for cell growth and survival. J. Immunol. Methods, 89, 271-277, 1986).

of proteins; the protein concentration of the cells was determined in accordance with Bradford (Bradford M. M. A rapid and sensitive method for the quantitation of microgram quantities of protein utilizing the principle of protein-dye binding. Anal. Biochem. (1977) vol 72, pp 248-254)

of glutathione (GSH), a peptide produced directly by the cell, for combating oxidative stress or various contaminants, such as, for example, heavy metals. Its synthesis requires ATP as energy source. GSH was determined in accordance with Hissin (Hissin P. J., Hilf R. A fluorometric method for determination of oxidised and reduced Glutathione in tissues. Analytical Biochemistry (1977) vol 74, pp 214-226).

Glutathione (GSH) is a peptide which is produced by cells in order to protect the cell against oxidative stress or heavy metals, such as, for example, lead or mercury. The three amino acids which are involved in the reduced form of GSH are in turn joined to specific cytoplasmatic enzymes which require ATP.

The increase in the GSH level has a positive influence on the activity of the glutathione-S-transferase, which represents a decontaminating enzyme.

Method: Human fibroblasts were inoculated in a nutrient medium (DMEM=Dulbecco Minimum Essential Medium from Life Technologie Sarl) with 10% fetal calf serum (from Dutcher) and incubated for 24 hours at 37° C. in a 5% CO$_2$ atmosphere.

The medium was then replaced by a suboptimum medium (without SVF), which comprised various extracts in varying concentrations (0.01; 0.03 and 0.1% by weight) in accordance with the description of the invention.

The results are given relative to an extract-free formulation for protein, MTT and GSH in the ratio and expressed as a percentage relative to the untreated control agent given as average value +/−SEM (error type of the average).

TABLE 4

Cell survival test (results in % based on the control without extract (average of 2 assays in triple determination)

| | Concentration in % by weight | MTT | Proteins | GSH/ proteins |
|---|---|---|---|---|
| Control | 0 | 100 | 100 | 100 |
| Extract as in example 3 | 0.03 | 108 | 104 | 107 |
| | 0.1 | 100 | 102 | 152 |
| Extract as in example 4 | 0.01 | 99 | 90 | 128 |
| | 0.03 | 118 | 91 | 263 |

The table gives in each case the mitochondrial activity via the MTT, protein contents and the GSH contents which were measured after three days for various concentrations of extracts. A fraction of native proteins of *Argania spinosa* as in example 4 with a concentration of 0.03% by weight has, according to this, significantly increased the mitochondrial activity (+18%). A fraction of native proteins from *Argania spinosa* as in example 4 with a concentration of only 0.03% is able to increase the GSH content in human fibroblasts by 163%.

These results show that the original or hydrolyzed protein extracts of *Argania spinosa* are highly capable of improving the metabolism (synthesis of proteins and of glutathione) by the human fibroblasts, which clearly gives rise to an energy-donating, stimulating and "antiaging" activity of these extracts.

8. Example

Cell Protective Action Against UVA on Human Fibroblasts Cultivated In Vitro

Background: UVA rays penetrate into the dermis where they lead to oxidative stress, which is detected by lipoperoxidation of the cytoplasma membranes.

The lipoperoxides are degraded to malonaldialdehyde, which will crosslink many biological molecules such as proteins and nucleic bases (enzyme inhibition or mutagenesis).

Glutathione (GSH) is a peptide which is produced directly by the cells in order to counteract oxidative stress or harmful environmental influences, such as, for example, increased mercury or lead content. The content of GSH was determined in accordance with the Hissin method, described in Anal. Biochem., 74, 214-226, 1976.

Method: To carry out these tests, a defined culture medium (DMEM) with 10% fetal calf serum was inoculated with the fibroblasts, and the plant extract (in the defined medium with 2% serum) was added 72 hours after inoculation.

Following incubation for 48 hours at 37° C. and a $CO_2$ content of 5%, the culture medium was replaced by a sodium chloride solution, and the fibroblasts were irradiated with a UVA dose (20 J/cm$^2$; tubes: MAZDA FLUOR TFWN40).

When the irradiation was complete, the content of cell proteins and the proportion of GSH was determined, and the MDA level (malonaldialdehyde level) in the supernatant saline solution was determined quantitatively by reaction with thiobarbituric acid. The results are given as a percentage compared with the control without irradiation.

TABLE 5

Quantification of malonaldialdehyde, cell proteins and GSH in fibroblasts (results in % based on the control, average value from 2 experiments, each with three repetitions)

| Concentration (% by wt.) | MDA level | Content of cell proteins | Content of GSH |
|---|---|---|---|
| Control without UVA | 0 | 100 | 100 |
| UVA (20 J/cm$^2$) | 100 | 105 | 74 |
| UVA + extract as in example 3 0.003% | 52 | 121 | 97 |

The results from table 5 show that the extracts from the plant *Argania spinosa* according to the invention significantly reduce the degree of MDA in human fibroblasts which is induced by UVA rays. Furthermore, there is high activity for keeping the content of GSH in human fibroblasts relatively constant following irradiation with UVA radiation. These results show a high capacity of protein fractions from *Argania spinosa* for reducing harmful effects of oxidative stress on the skin.

9. Example

Antiinflammatory Properties In Vitro-UVB Light Protection

Cell Protection Effect Against UVB on In Vitro Cultivated Human Keratinocytes

Background: UVB rays (from 280 to 320 nm) trigger inflammation (erythema, odema) by activating an enzyme, namely phospholipase A2 or PLA2, which removes arachidonic acid from the phospholipids of the plasma membrane. Arachidonic acid is the precursor of prostaglandins, which cause inflammation and cell membrane damage; the prostaglandins E2 (=PGE2) are formed by cyclooxygenase. This membrane stress is indicated by the release of the cytoplasm enzyme lactate dehydrogenase (LDH). The effect of UVB radiation was investigated on keratinocytes in vitro by determining the release of the cytoplasm enzyme LDH (lactate dehydrogenase). This enzyme serves as a marker for cell damage.

Method: To carry out the tests, a defined medium (DMEM), which comprises 10% fetal calf serum, was inoculated with the keratinocytes and the plant extract (diluted with saline solution) was added 72 hours after inoculation.

The keratinocytes were then irradiated with a UVB dose (50 mJ/cm$^2$-tubes: DUKE GL40E).

Following further incubation for 1 day at 37° C. and at 5% $CO_2$, the LDH and the PGE2 content in the supernatant was determined. The content of LDH (lactate dehydrogenase) was determined by means of an enzyme reaction (kit used to investigate the LDH content from Roche). The content of PGE2 was determined using an ELISA test (ELISA kit from Roche). Following trypsin treatment, the cells were centrifuged and counted.

TABLE 6

Cell protection effect leaf extract of Argania spinosa against UVB rays; results in % based on the control, average value from 2 experiments, each with two repetitions

| Extract as in example 1 | Number of keratinocytes (%) | Content of PGE2 (%) | Content of released LDH (%) |
|---|---|---|---|
| Control without UV | 100 | 0 | 0 |
| Control with UVB (50 mJ/cm$^2$) | 37 | 100 | 100 |
| UVB + extract as in example 3 0.03% | 41 | 61 | 83 |

The results of this test prove that a protein fraction of the plant *Argania spinosa* according to the invention reduces the effect of UVB radiation on the number of keratinocytes. A reduction in the content of released LDH in the cytoplasm and a reduction in the PGE2 content were found. The protein extracts described, accordingly, exhibit the ability to reduce the damage to cell membranes caused by UVB radiation and show an inhibiting effect against inflammations which are induced by UVB radiation.

10. Example

Determination of the Enzymatic Activity of the Glucose-6-Phosphate Dehydrogenase Background: The aim of this test is to investigate the stimulating properties on the enzymatic activity of glucose-6-phosphate dehydrogenase (G6PDH), which can accelerate skin aging. Glucose-6-phosphate dehydrogenase catalyzes the first step of the oxidative branch of the pentose phosphate pathway. In this first step, glucose-6-phosphate is oxidized to 6-phosphono-δ-lactone under the action of NADP. This coenzyme is reduced in this oxidation to NADPH2. The reduced form of this coenzyme can catalyze many enzymatic reactions, such as, for example, recycling of glutathione or lipid synthesis. Furthermore, the pentose phosphate pathway produces an essential component for the construction of the DNA, deoxyribose. Reduced glutathione protects many enzymes with the "SH" group and thus promotes the ability of the cell to survive against oxidative stress, such as, for example, UV radiation. For the reasons given, G6PDH is a very important enzyme for the regeneration of the skin, for the synthesis of essential substances and for the protection of the cells against oxidative stress.

The G6PDH activity was determined in accordance with the process described by Natsuko Okada and Yukio Kitano in: Arch. Dermatol. Res., 271 (3): 341-346, 1981, by in vitro determination of the enzymatic activity of glucose-6-phosphate dehydrogenase in human fibroblasts.

The DNA content was determined in accordance with the method described by Desaulniers in Toxic, in vitro 12(4), 409-422 (1998). The incubation time of the fibroblasts was in each case 3 days and 6 days. The results are summarized in table 7. In each case, the average of 8 experiments with triple determination is given.

TABLE 7

G6PDH activity and DNA - data in rel. %

| Substance used | Conc. % by wt. | DNA content after 3 days rel. % | G6PDH activity after 3 days rel. % | DNA content after 6 days rel. % | G6PDH activity after 6 days rel. % |
|---|---|---|---|---|---|
| Control | 0 | 100 | 100 | 100 | 100 |
| Extract as in example 3 | 0.1 | 117 | 133 | 50 | 254 |
|  | 0.3 | 112 | 165 | 56 | 319 |
| Extract as in example 4 | 0.01 | 90 | 112 | 76 | 142 |
|  | 0.03 | 108 | 119 | 41 | 191 |
| Retinoic acid | 0.0003 mM | 98 | 97 | 60 | 120 |
|  | 0.001 mM | 88 | 89 | 44 | 128 |

The results in table 7 show that the protein fraction from the plant *Argania spinosa* with a concentration of 0.03 and 0.1% by weight has considerably increased the activity of G6PDH in human fibroblasts after 6 days. Using this test, it can be proven that the protein fractions from the residues of oil production from *Argania spinosa* have a high potential for protecting human skin against stress, such as, for example, UV, environmental contamination, or for being effective against skin aging.

11. Example

Formulations of Cosmetic Compositions Comprising Native from Proteins Extracts from the Plant *Argania spinosa*

The extracts obtained as in example 1 to 4 were used in the following formulations K1 to K21 according to the invention, and also 1 to 30. The cosmetic compositions prepared in this way displayed, compared with the comparison formulations C1, C2 and C3, very good skin care properties with simultaneously good skin compatibility. Moreover, the compositions according to the invention are stable against oxidative decomposition.

All of the substances with a registered trade name ® used and listed in table 3-6 are trademarks and products of the COGNIS group.

TABLE 8

Soft cream formulations K1 to K7
(All data in % by weight based on the cosmetic composition)

| INCI name | K1 | K2 | K3 | K4 | K5 | K6 | K7 | C1 |
|---|---|---|---|---|---|---|---|---|
| Glyceryl Stearate (and) Ceteareth 12/20 (and) Cetearyl Alcohol (and) Cetyl Palmitate | 8.0 | 8.0 | 8.0 | 8.0 | 8.0 | 8.0 | 8.0 | 8.0 |
| Cetearyl Alcohol | 2.0 | 2.0 | 2.0 | 2.0 | 2.0 | 2.0 | 2.0 | 2.0 |
| Dicaprylyl Ether | 2.0 | 2.0 | 2.0 | 2.0 | 2.0 | 2.0 | 2.0 | 2.0 |
| Cocoglycerides | 3.0 | 3.0 | 3.0 | 3.0 | 3.0 | 3.0 | 3.0 | 3.0 |
| Cetearyl Isononanoate | 3.0 | 3.0 | 3.0 | 3.0 | 3.0 | 3.0 | 3.0 | 3.0 |
| Glycerol (86% strength by wt.) | 3.0 | 3.0 | 3.0 | 3.0 | 3.0 | 3.0 | 3.0 | 3.0 |
| Extract as in example 1 to 4 | 0.5 | 0.5 | 0.5 | 0.5 | 0.5 | 0.5 | 0.5 | — |
| Tocopherol |  | 0.5 |  |  |  |  |  |  |
| Allantoin |  |  | 0.2 |  |  |  |  |  |
| Bisabolol |  |  |  | 0.5 |  |  |  |  |

TABLE 8-continued

Soft cream formulations K1 to K7
(All data in % by weight based on the cosmetic composition)

| INCI name | K1 | K2 | K3 | K4 | K5 | K6 | K7 | C1 |
|---|---|---|---|---|---|---|---|---|
| Chitosan (Hydagen CMF) | | | | | 10.0 | | | |
| Deoxyribonucleic acid[1)] | | | | | | 0.5 | | |
| Panthenol | | | | | | | 0.5 | |
| Water | | | | Ad 100 | | | | |

TABLE 9

Night cream formulations K8 to K14
(All data in % by weight based on the cosmetic composition)

| INCI name | K8 | K9 | K10 | K11 | K12 | K13 | K14 | C2 |
|---|---|---|---|---|---|---|---|---|
| Polyglyceryl-2 Dipolyhydroxystearate | 4.0 | 4.0 | 4.0 | 4.0 | 4.0 | 4.0 | 4.0 | 5.0 |
| Polyglyceryl-3 Diisostearate | 2.0 | 2.0 | 2.0 | 2.0 | 2.0 | 2.0 | 2.0 | 2.0 |
| Cera Alba | 2.0 | 2.0 | 2.0 | 2.0 | 2.0 | 2.0 | 2.0 | 2.0 |
| Zinc Stearate | 2.0 | 2.0 | 2.0 | 2.0 | 2.0 | 2.0 | 2.0 | 2.0 |
| Cocoglycerides | 3.0 | 3.0 | 3.0 | 3.0 | 3.0 | 3.0 | 3.0 | 3.0 |
| Cetearyl Isononanoate | 8.0 | 8.0 | 8.0 | 8.0 | 8.0 | 8.0 | 8.0 | 8.0 |
| Dicaprylyl Ether | 5.0 | 5.0 | 5.0 | 5.0 | 5.0 | 5.0 | 5.0 | 5.0 |
| Magnesium Sulfate | 1.0 | 1.0 | 1.0 | 1.0 | 1.0 | 1.0 | 1.0 | 1.0 |
| Glycerol (86% strength by wt.) | 5.0 | 5.0 | 5.0 | 5.0 | 5.0 | 5.0 | 5.0 | 5.0 |
| Extract as in example 1 to 4 | 0.5 | 0.5 | 0.5 | 0.5 | 0.5 | 0.5 | 0.5 | — |
| Tocopherol | | 0.5 | | | | | | |
| Allantoin | | | | 0.2 | | | | |
| Bisabolol | | | | | | 0.5 | | |
| Chitosan (Hydagen CMF) | | | | | 10.0 | | | |
| Deoxyribonucleic acid[1)] | | | | | | 0.5 | | |
| Panthenol | | | | | | | 0.5 | |
| Water | | | | Ad 100 | | | | |

TABLE 10

W/O body lotion formulations K15 to K21
(All data in % by weight based on the cosmetic composition)

| INCI name | K15 | K16 | K17 | K18 | K19 | K20 | K21 | C3 |
|---|---|---|---|---|---|---|---|---|
| PEG-7 Hydrogenated Castor Oil | 7.0 | 7.0 | 7.0 | 7.0 | 7.0 | 7.0 | 7.0 | 7.0 |
| Decyl Oleate | 7.0 | 7.0 | 7.0 | 7.0 | 7.0 | 7.0 | 7.0 | 7.0 |
| Cetearyl Isononanoate | 7.0 | 7.0 | 7.0 | 7.0 | 7.0 | 7.0 | 7.0 | 7.0 |
| Glycerol (86% strength by wt.) | 5.0 | 5.0 | 5.0 | 5.0 | 5.0 | 5.0 | 5.0 | 5.0 |
| $MgSO_4 \cdot 7H_2O$ | 1.0 | 1.0 | 1.0 | 1.0 | 1.0 | 1.0 | 1.0 | 1.0 |
| Extract as in example 1 to 3 | 1.5 | 1.5 | 1.5 | 1.5 | 1.5 | 1.5 | 1.5 | — |
| Tocopherol | | 0.5 | | | | | | |
| Allantoin | | | 0.2 | | | | | |
| Bisabolol | | | | 0.5 | | | | |
| Chitosan (Hydagen CMF) | | | | | 10.0 | | | |
| Deoxyribonucleic acid[1)] | | | | | | 0.5 | | |
| Panthenol | | | | | | | 0.5 | |
| Water | | | | Ad 100 | | | | |

[1)] Deoxyribonucleic acid: molecular weight about 70 000, purity (determined by spectrophotometric measurement of the absorption at 260 nm and 280 nm): at least 1.7.

TABLE 11

Formulations
(All data in % by weight based on the cosmetic composition, water, preservatives make up to 100% by weight)
Cosmetic preparations (water, preservatives ad 100% by weight)

| Composition (INCI) | 1 | 2 | 3 | 4 | 5 | 6 | 7 | 8 | 9 | 10 |
|---|---|---|---|---|---|---|---|---|---|---|
| Texapon ® NSO Sodium Laureth Sulfate | — | — | — | — | — | — | 38.0 | 38.0 | 25.0 | — |

TABLE 11-continued

Formulations
(All data in % by weight based on the cosmetic composition,
water, preservatives make up to 100% by weight)
Cosmetic preparations (water, preservatives ad 100% by weight)

| | | | | | | | | | | |
|---|---|---|---|---|---|---|---|---|---|---|
| Texapon ® SB 3 Disodium Laureth Sulfosuccinate | — | — | — | — | — | — | — | — | 10.0 | — |
| Plantacare ® 818 Coco Glucosides | — | — | — | — | — | — | 7.0 | 7.0 | 6.0 | — |
| Plantacare ® PS 10 Sodium Laureth Sulfate (and) Coco Glucosides | — | — | — | — | — | — | — | — | — | 16.0 |
| Dehyton ® PK 45 Cocamidopropyl Betaine | — | — | — | — | — | — | — | — | 10.0 | — |
| Dehyquart ® A Cetrimonium Chloride | 2.0 | 2.0 | 2.0 | 2.0 | 4.0 | 4.0 | — | — | — | — |
| Dehyquart L ® 80 Dicocoylmethylethoxymonium Methosulfate (and) Propylene Glycol | 1.2 | 1.2 | 1.2 | 1.2 | 0.6 | 0.6 | — | — | — | — |
| Eumulgin ® B2 Ceteareth-20 | 0.8 | 0.8 | — | 0.8 | — | 1.0 | — | — | — | — |
| Eumulgin ® VL 75 Lauryl Glucoside (and) Polyglyceryl-2 Polyhydroxystearate (and) Glycerin | — | — | 0.8 | — | 0.8 | — | — | — | — | — |
| Lanette ® O Cetearyl Alcohol | 2.5 | 2.5 | 2.5 | 2.5 | 3.0 | 2.5 | — | — | — | — |
| Cutina ® GMS Glyceryl Stearate | 0.5 | 0.5 | 0.5 | 0.5 | 0.5 | 1.0 | — | — | — | — |
| Cetiol ® HE PEG-7 Glyceryl Cocoate | 1.0 | — | — | — | — | — | — | — | 1.0 | — |
| Cetiol ® PGL Hexyldecanol (and) Hexyldecyl Laurate | — | 1.0 | — | — | 1.0 | — | — | — | — | — |
| Cetiol ® V Decyl Oleate | — | — | — | 1.0 | — | — | — | — | — | — |
| Eutanol ® G Octyldodecanol | — | — | 1.0 | — | — | 1.0 | — | — | — | — |
| Nutrilan ® Keratin W Hydrolyzed Keratin | — | — | — | 2.0 | — | — | — | — | — | — |
| Lamesoft ® LMG Glyceryl Laurate (and) Potassium Cocoyl Hydrolyzed Collagen | — | — | — | — | — | — | 3.0 | 2.0 | 4.0 | — |
| Euperlan ® PK 3000 AM Glycol Distearate (and) Laureth-4 (and) Cocamidopropyl Betaine | — | — | — | — | — | — | — | 3.0 | 5.0 | 5.0 |
| Generol ® 122 N Soja Sterol | — | — | — | — | 1.0 | 1.0 | — | — | — | — |
| Extract as in example 1-4 | 1.0 | 1.0 | 1.0 | 1.0 | 1.0 | 1.0 | 1.0 | 1.0 | 1.0 | 1.0 |
| Hydagen ® CMF Chitosan | 1.0 | 1.0 | 1.0 | 1.0 | 1.0 | 1.0 | 1.0 | 1.0 | 1.0 | 1.0 |
| Copherol ® 12250 Tocopherol Acetate | — | — | 0.1 | 0.1 | — | — | — | — | — | — |
| Arlypon ® F Laureth-2 | — | — | — | — | — | — | 3.0 | 3.0 | 1.0 | — |
| Sodium Chloride | — | — | — | — | — | — | — | 1.5 | — | 1.5 |

| Composition (INCI) | 11 | 12 | 13 | 14 | 15 | 16 | 17 | 18 | 19 | 20 |
|---|---|---|---|---|---|---|---|---|---|---|
| Texapon ® NSO Sodium Laureth Sulfate | 20.0 | 20.0 | 12.4 | — | 25.0 | 11.0 | — | — | — | — |
| Texapon ® K 14 S | — | — | — | — | — | — | — | — | 11.0 | 23.0 |

TABLE 11-continued

Formulations
(All data in % by weight based on the cosmetic composition,
water, preservatives make up to 100% by weight)
Cosmetic preparations (water, preservatives ad 100% by weight)

| Ingredient | | | | | | | | | | |
|---|---|---|---|---|---|---|---|---|---|---|
| Sodium Myreth Sulfate Texapon ® SB 3 | — | — | — | — | — | 7.0 | — | — | — | — |
| Disodium Laureth Sulfosuccinate Plantacare ® 818 | 5.0 | 5.0 | 4.0 | — | — | — | — | — | 6.0 | 4.0 |
| Coco Glucosides Plantacare ® 2000 | — | — | — | — | 5.0 | 4.0 | — | — | — | — |
| Decyl Glucoside Plantacare ® PS 10 | — | — | — | 40.0 | — | — | 16.0 | 17.0 | — | — |
| Sodium Laureth Sulfate (and) Coco Glucosides Dehyton ® PK 45 | 20.0 | 20.0 | — | — | 8.0 | — | — | — | — | 7.0 |
| Cocamidopropyl Betaine Eumulgin ® B1 | — | — | — | — | 1.0 | — | — | — | — | — |
| Ceteareth-12 Eumulgin ® B2 | — | — | — | 1.0 | — | — | — | — | — | — |
| Ceteareth-20 Lameform ® TGI | — | — | — | 4.0 | — | — | — | — | — | — |
| Polyglyceryl-3 Isostearate Dehymuls ® PGPH | — | — | 1.0 | — | — | — | — | — | — | — |
| Polyglyceryl-2 Dipolyhydroxystearate Monomuls ® 90-L 12 | — | — | — | — | — | — | — | — | 1.0 | 1.0 |
| Glyceryl Laurate Cetiol ® HE | — | 0.2 | — | — | — | — | — | — | — | — |
| PEG-7 Glyceryl Cocoate Eutanol ® G | — | — | — | 3.0 | — | — | — | — | — | — |
| Octyldodecanol Nutrilan ® Keratin W | — | — | — | — | — | — | — | — | 2.0 | 2.0 |
| Hydrolyzed Keratin Nutrilan ® I | 1.0 | — | — | — | — | 2.0 | — | 2.0 | — | — |
| Hydrolyzed Collagen Lamesoft ® LMG | — | — | — | — | — | — | — | — | 1.0 | — |
| Glyceryl Laurate (and) Potassium Cocoyl Hydrolyzed Collagen Lamesoft ® 156 | — | — | — | — | — | — | — | — | — | 5.0 |
| Hydrogenated Tallow Glyceride (and) Potassium Cocoyl Hydrolyzed Collagen Gluadin ® WK | 1.0 | 1.5 | 4.0 | 1.0 | 3.0 | 1.0 | 2.0 | 2.0 | 2.0 | — |
| Sodium Cocoyl Hydrolyzed Wheat Protein Euperlan ® PK 3000 AM | 5.0 | 3.0 | 4.0 | — | — | — | — | 3.0 | 3.0 | — |
| Glycol Distearate (and) Laureth-4 (and) Cocamidopropyl Betaine Panthenol | — | — | 1.0 | — | — | — | — | — | — | — |
| Arlypon ® F | 2.6 | 1.6 | — | 1.0 | 1.5 | — | — | — | — | — |
| Laureth-2 Extract as in example 1-4 | 1.0 | 1.0 | 1.0 | 1.0 | 1.0 | 1.0 | 1.0 | 1.0 | 1.0 | 1.0 |
| Hydagen ® CMF Chitosan | 1.0 | 1.0 | 1.0 | 1.0 | 1.0 | 1.0 | 1.0 | 1.0 | 1.0 | 1.0 |
| Sodium Chloride | — | — | — | — | — | 1.6 | 2.0 | 2.2 | — | 3.0 |

TABLE 11-continued

Formulations
(All data in % by weight based on the cosmetic composition,
water, preservatives make up to 100% by weight)
Cosmetic preparations (water, preservatives ad 100% by weight)

| | | | | | | | | | | |
|---|---|---|---|---|---|---|---|---|---|---|
| Glycerol (86% strength by weight) | — | 5.0 | — | — | — | — | — | 1.0 | 3.0 | — |

| Composition (INCI) | 21 | 22 | 23 | 24 | 25 | 26 | 27 | 28 | 29 | 30 |
|---|---|---|---|---|---|---|---|---|---|---|
| Texapon ® NSO Sodium Laureth Sulfate | — | 30.0 | 30.0 | — | 25.0 | — | — | — | — | — |
| Plantacare ® 818 Coco Glucosides | — | 10.0 | — | — | 20.0 | — | — | — | — | — |
| Plantacare ® PS 10 Sodium Laureth Sulfate (and) Coco Glucosides | 22.0 | — | 5.0 | 22.0 | — | — | — | — | — | — |
| Dehyton ® PK 45 Cocamidopropyl Betaine | 15.0 | 10.0 | 15.0 | 15.0 | 20.0 | — | — | — | — | — |
| Emulgade ® SE Glyceryl Stearate (and) Ceteareth 12/20 (and) Cetearyl Alcohol (and) Cetyl Palmitate | — | — | — | — | — | 5.0 | 5.0 | 4.0 | — | — |
| Eumulgin ® B1 Ceteareth-12 | — | — | — | — | — | — | — | 1.0 | — | — |
| Lameform ® TGI Polyglyceryl-3 Isostearate | — | — | — | — | — | — | — | — | 4.0 | — |
| Dehymuls ® PGPH Polyglyceryl-2 Dipolyhydroxystearate | — | — | — | — | — | — | — | — | — | 4.0 |
| Monomuls ® 90-O 18 Glyceryl Oleate | — | — | — | — | — | — | — | — | 2.0 | — |
| Cetiol ® HE PEG-7 Glyceryl Cocoate | 2.0 | — | — | 2.0 | 5.0 | — | — | — | — | 2.0 |
| Cetiol ® OE Dicaprylyl Ether | — | — | — | — | — | — | — | — | 5.0 | 6.0 |
| Cetiol ® PGL Hexyldecanol (and) Hexyldecyl Laurate | — | — | — | — | — | — | — | 3.0 | 10.0 | 9.0 |
| Cetiol ® SN Cetearyl Isononanoate | — | — | — | — | — | 3.0 | 3.0 | — | — | — |
| Cetiol ® V Decyl Oleate | — | — | — | — | — | 3.0 | 3.0 | — | — | — |
| Myritol ® 318 Coco Caprylate Caprate | — | — | — | — | — | — | — | 3.0 | 5.0 | 5.0 |
| Beeswax | — | — | — | — | — | — | — | — | 7.0 | 5.0 |
| Nutrilan ® Elastin E20 Hydrolyzed Elastin | — | — | — | — | — | 2.0 | — | — | — | — |
| Nutrilan ® I-50 Hydrolyzed Collagen | — | — | — | — | 2.0 | — | 2.0 | — | — | — |
| Gluadin ® AGP Hydrolyzed Wheat Gluten | 0.5 | 0.5 | 0.5 | — | — | — | — | 0.5 | — | — |
| Gluadin ® WK Sodium Cocoyl Hydrolyzed Wheat Protein | 2.0 | 2.0 | 2.0 | 2.0 | 5.0 | — | — | — | 0.5 | 0.5 |
| Euperlan ® PK 3000 AM Glycol Distearate (and) Laureth-4 (and) Cocamidopropyl Betaine | 5.0 | — | — | 5.0 | — | — | — | — | — | — |
| Arlypon ® F Laureth-2 | — | — | — | — | — | — | — | — | — | — |
| Extract as in example 1-4 | 1.0 | 1.0 | 1.0 | 1.0 | 1.0 | 1.0 | 1.0 | 1.0 | 1.0 | 1.0 |

TABLE 11-continued

Formulations
(All data in % by weight based on the cosmetic composition,
water, preservatives make up to 100% by weight)
Cosmetic preparations (water, preservatives ad 100% by
weight)

| | | | | | | | | | | |
|---|---|---|---|---|---|---|---|---|---|---|
| Hydagen ® CMF Chitosan | 1.0 | 1.0 | 1.0 | 1.0 | 1.0 | 1.0 | 1.0 | 1.0 | 1.0 | 1.0 |
| Magnesium Sulfate Hepta Hydrate | — | — | — | — | — | — | — | — | 1.0 | 1.0 |
| Glycerol (86% strength by weight) | — | — | — | — | — | 3.0 | 3.0 | 5.0 | 5.0 | 3.0 |

(1-4) hair rinse,
(5-6) hair treatment,
(7-8) shower preparation,
(9) shower gel,
(10) washing lotion
(11-14) two-in-one shower preparation,
(15-20) shampoo
(21-25) foam bath,
(26) soft cream,
(27, 28) moisturizing emulsion,
(29, 30) night cream

The invention claimed is:

1. A composition selected from the group consisting of cosmetic compositions and dermapharmaceutical compositions, comprising a mixture containing native proteins from the plant *Argania spinosa* wherein said native proteins have a molecular weight of at least about 10,000 Da, and wherein the mixture containing the native proteins is present in the composition in an amount of about 0.03 to 5% by weight, based on a dry weight of the composition.

2. The composition of claim 1 wherein the mixture containing the native proteins is present in the composition in an amount of about 0.03 to 0.6% by weight, based on a dry weight of the composition.

3. A process for both protecting, and enhancing the appearance of at least one member selected from the group consisting of, skin and hair comprising contacting the at least one member with a composition comprising a mixture containing an effective amount of native proteins from the plant *Argania spinosa*, wherein, the native proteins have a molecular weight of at least about 10,000 Da.

4. The process of claim 3 wherein the mixture containing native proteins is obtained from seeds and/or defatted seeds of the plant *Argania spinosa*.

5. The process of claim 3 wherein the mixture containing native proteins is obtained by extraction of at least a portion of the plant *Argania spinosa* with an aqueous medium at a pH of less than or equal to 12 and a temperature of from 20° C. to 100° C.

6. The process of claim 3 wherein the native proteins have a molecular weight of from 10,000 Da to about 250,000 Da.

7. The process of claim 3 wherein the native proteins comprise a native protein having a molecular weight of from 10,000 to 18,000 Da.

8. The process of claim 3 wherein the native proteins comprise native proteins having a molecular weight of from 170,000 to 250,000 Da.

9. The process of claim 3 wherein the mixture comprising native proteins has an active substance content of about 20 to 85% by weight, based on a dry weight of the mixture.

10. The process of claim 3 wherein the mixture comprising native proteins is present in the composition, in an amount of about 0.01 to 25% by weight, based on a weight of the composition.

11. The process of claim 3 wherein the mixture comprising native proteins is present in the composition in an amount of about 0.03 to 5% by weight, based on a weight of the composition.

12. The process of claim 3 wherein the mixture comprising native proteins is present in the composition in an amount of about 0.03 to 0.6% by weight, based on a weight of the composition.

* * * * *